(12) United States Patent
Pfitzner et al.

(10) Patent No.: US 7,226,747 B2
(45) Date of Patent: Jun. 5, 2007

(54) METHOD OF IDENTIFYING SUBSTANCES WHICH MODULATE INTERLEUKIN 4(IL-4) SIGNALING

(75) Inventors: Edith Pfitzner, Frankfurt am Main (DE); Claudia Monika Litterst, Frankfurt am Main (DE)

(73) Assignee: Boehringer Ingelheim Corporation, Ingelheim (DE)

( * ) Notice: Subject to any disclaimer, the term of this patent is extended or adjusted under 35 U.S.C. 154(b) by 744 days.

(21) Appl. No.: 10/190,866

(22) Filed: Jul. 8, 2002

(65) Prior Publication Data
US 2003/0092619 A1    May 15, 2003

Related U.S. Application Data

(60) Provisional application No. 60/306,552, filed on Jul. 19, 2001.

(30) Foreign Application Priority Data
Jul. 13, 2001  (EP)  ................... 01117097

(51) Int. Cl.
*G01N 33/53* (2006.01)
*C12Q 1/00* (2006.01)

(52) U.S. Cl. ............... 435/7.1; 435/4; 435/7.8; 435/7.9

(58) Field of Classification Search .............. None
See application file for complete search history.

(56) References Cited

FOREIGN PATENT DOCUMENTS

WO   WO 99 10493 A   3/1999
WO   WO 99 41608     8/1999
WO   WO 99 50283     10/1999

OTHER PUBLICATIONS

Rudlinger et al, Characteristics of amino acids as components of a peptide hormone sequence, Peptide Hormone, Oct. 29, 1976, p. 1-7.*
Svaren, J. et al: "The Nab2 and Stat6 genes share a common transcription termination region" Genomics, 1997, 41(1):33-39.
Abstract XP-002228754 "STAT 6 (Fragment)".
Litterst, et al; "Transcriptional Activation by STAT6 Requires the Direct Interaction with NCoA-1*"; J. Biol. Chem., vol. 276, No. 49; 2001; p. 45713-45721.

* cited by examiner

*Primary Examiner*—Robert S. Landsman
*Assistant Examiner*—Bruce D. Hissong
(74) *Attorney, Agent, or Firm*—Michael Morris; Mary-Ellen M. Devlin; Anthony P. Bottino

(57) ABSTRACT

The present invention relates to a method to identify substances and a use of such substances which can modulate IL-4 dependent signaling involved in tumor diseases, preferably Hodgkin Lymphomas or inflammatory airway diseases, preferably asthma and a method for determining whether a substance can modulate the interaction of STAT6 with NCoA-1, characterized in that
 a) STAT6 or fragments or derivatives thereof having the ability to bind to NcoA-1 are brought into contact with NCoA-1 or fragments or derivatives of NCoA-1 having the ability to bind STAT6 under conditions where STAT6 and NCoA-1 or fragments or derivatives thereof are capable of forming a complex, and the complex can be used to induce a measurable readout;
 b) a readout is measured in the absence or presence of the substance of interest;
 c) the readout in absence of substance of interest is compared with readout in presence of substance of interest.

13 Claims, 12 Drawing Sheets

Figure 1:
Figure 1:
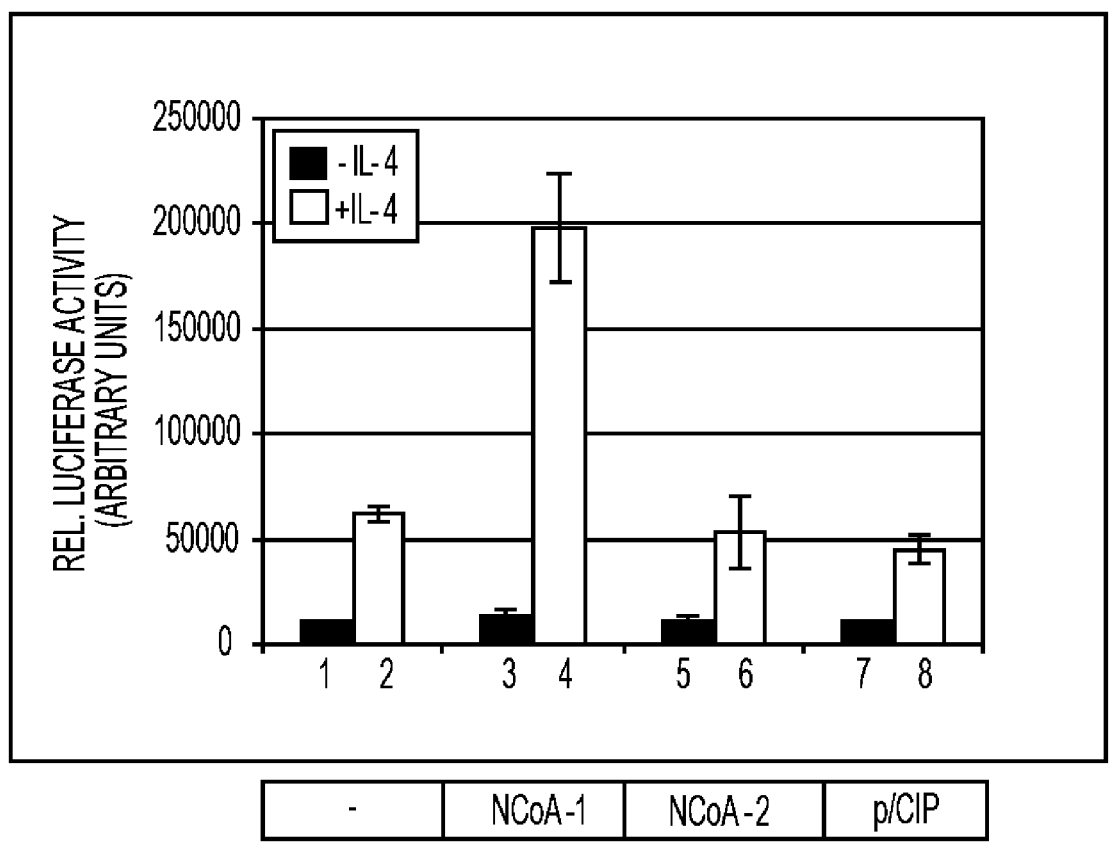

PEPTIDE 1  
794                    814  
LLPPTEQDLTKLLLEGQGESG
          *   *  
-ATKAL-   MUTATIONS  
802  805   L802,805 TO A
FIG. 10A
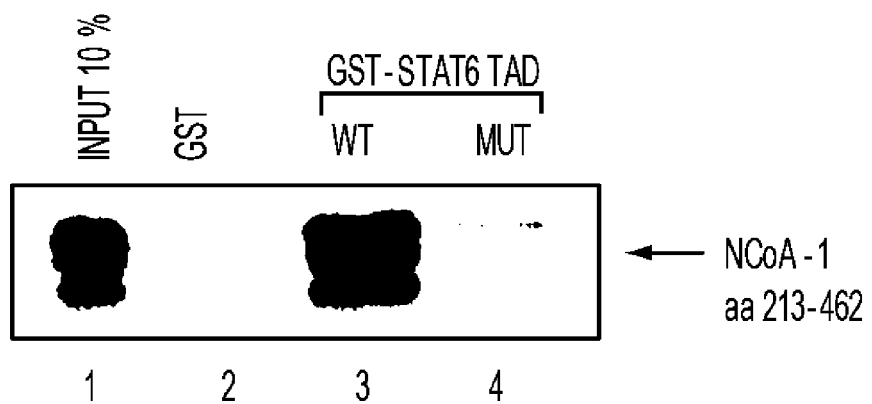
FIG. 10B
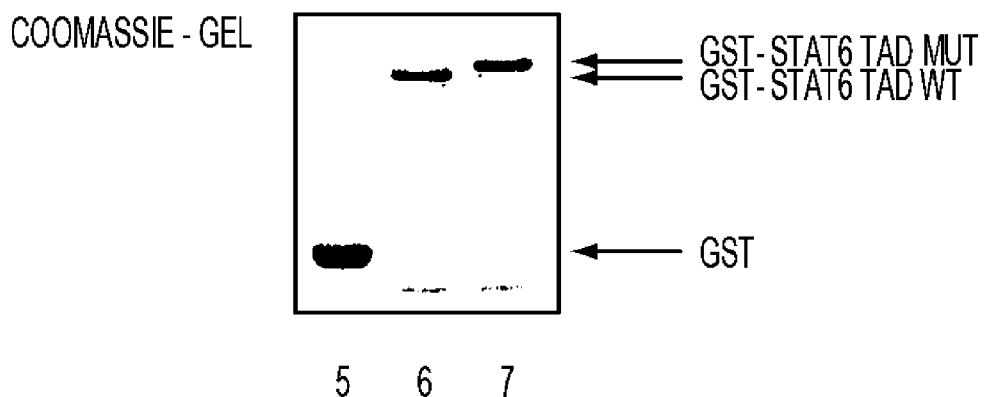
FIG. 10C

SEQUENCE LISTING

```
<160> NUMBER OF SEQ ID NOS: 6
<210> SEQ ID NO 1
<211> LENGTH: 401
<212> TYPE: PRT
<213> ORGANISM: Artificial Sequence
<220> FEATURE:
<223> OTHER INFORMATION: Description of Artificial Sequence: derivative
      of STAT6 fragment

<400> SEQUENCE: 1

Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190
```

```
Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Ile Glu Gly
210                 215                 220

Arg Gly Ile Pro Glu Phe Asp Ser Ser Met Ser Met Gln Leu Gly Pro
225                 230                 235                 240

Asp Met Val Pro Gln Val Tyr Pro Pro His Ser His Ser Ile Pro Pro
                245                 250                 255

Tyr Gln Gly Leu Ser Pro Glu Glu Ser Val Asn Val Leu Ser Ala Phe
            260                 265                 270

Gln Glu Pro His Leu Gln Met Pro Pro Ser Leu Gly Gln Met Ser Leu
            275                 280                 285

Pro Phe Asp Gln Pro His Pro Gln Gly Leu Leu Pro Cys Gln Pro Gln
290                 295                 300

Glu His Ala Val Ser Ser Pro Asp Pro Leu Leu Cys Ser Asp Val Thr
305                 310                 315                 320

Met Val Glu Asp Ser Cys Leu Ser Gln Pro Val Thr Ala Phe Pro Gln
                325                 330                 335

Gly Thr Trp Ile Gly Glu Asp Ile Phe Pro Pro Leu Leu Pro Pro Thr
            340                 345                 350

Glu Gln Asp Leu Thr Lys Leu Leu Leu Glu Gly Gln Gly Glu Ser Gly
            355                 360                 365

Gly Gly Ser Leu Gly Ala Gln Pro Leu Leu Gln Pro Ser His Tyr Gly
370                 375                 380

Gln Ser Gly Ile Ser Met Ser His Met Asp Leu Arg Ala Asn Pro Ser
385                 390                 395                 400

Trp

<210> SEQ ID NO 2
<211> LENGTH: 171
<212> TYPE: PRT
<213> ORGANISM: Homo sapiens

<400> SEQUENCE: 2

Asp Ser Ser Met Ser Met Gln Leu Gly Pro Asp Met Val Pro Gln Val
 1               5                  10                  15

Tyr Pro Pro His Ser His Ser Ile Pro Pro Tyr Gln Gly Leu Ser Pro
            20                  25                  30

Glu Glu Ser Val Asn Val Leu Ser Ala Phe Gln Glu Pro His Leu Gln
            35                  40                  45

Met Pro Pro Ser Leu Gly Gln Met Ser Leu Pro Phe Asp Gln Pro His
        50                  55                  60

Pro Gln Gly Leu Leu Pro Cys Gln Pro Gln Glu His Ala Val Ser Ser
65                  70                  75                  80

Pro Asp Pro Leu Leu Cys Ser Asp Val Thr Met Val Glu Asp Ser Cys
                85                  90                  95

Leu Ser Gln Pro Val Thr Ala Phe Pro Gln Gly Thr Trp Ile Gly Glu
            100                 105                 110

Asp Ile Phe Pro Pro Leu Leu Pro Pro Thr Glu Gln Asp Leu Thr Lys
            115                 120                 125

Leu Leu Leu Glu Gly Gln Gly Glu Ser Gly Gly Gly Ser Leu Gly Ala
130                 135                 140
```

```
Gln Pro Leu Leu Gln Pro Ser His Tyr Gly Gln Ser Gly Ile Ser Met
145                 150                 155                 160

Ser His Met Asp Leu Arg Ala Asn Pro Ser Trp
                165                 170

<210> SEQ ID NO 3
<211> LENGTH: 310
<212> TYPE: PRT
<213> ORGANISM: Artificial Sequence
<220> FEATURE:
<223> OTHER INFORMATION: Description of Artificial Sequence: derivative
      of NCoA-1 fragment

<400> SEQUENCE: 3

Met His His His His His Ser Ser Gly Leu Val Pro Arg Gly Ser
1               5                   10                  15

Gly Met Lys Glu Thr Ala Ala Lys Phe Glu Arg Gln His Met Asp
                20                  25                  30

Ser Pro Asp Leu Gly Thr Asp Asp Asp Lys Ala Met Gly Tyr Leu
                35                  40                  45

Trp Ile Gln Glu Ala Cys Gln Arg Tyr Glu Val Met Gln Cys Phe Thr
    50                  55                  60

Val Ser Gln Pro Lys Ser Ile Gln Glu Asp Gly Glu Asp Phe Gln Ser
65                  70                  75                  80

Cys Leu Ile Cys Ile Ala Arg Arg Leu Pro Arg Pro Ala Ile Thr
                85                  90                  95

Gly Val Glu Ser Phe Met Thr Lys Gln Asp Thr Thr Gly Lys Ile Ile
                100                 105                 110

Ser Ile Asp Thr Ser Ser Leu Arg Ala Ala Gly Arg Thr Gly Trp Glu
                115                 120                 125

Asp Leu Val Arg Lys Cys Ile Tyr Ala Phe Phe Gln Pro Gln Gly Arg
130                 135                 140

Glu Pro Ser Tyr Ala Arg Gln Leu Phe Gln Glu Val Met Thr Arg Gly
145                 150                 155                 160

Thr Ala Ser Ser Pro Ser Tyr Arg Phe Ile Leu Asn Asp Gly Thr Met
                165                 170                 175

Leu Ser Ala His Thr Lys Cys Lys Leu Cys Tyr Pro Gln Ser Pro Asp
                180                 185                 190

Met Gln Pro Phe Ile Met Gly Ile His Ile Ile Asp Arg Glu His Ser
                195                 200                 205

Gly Leu Ser Pro Gln Asp Asp Ser Asn Ser Gly Met Ser Ile Pro Arg
                210                 215                 220

Ile Asn Pro Ser Val Asn Pro Gly Ile Ser Pro Ala His Gly Val Thr
225                 230                 235                 240

Arg Ser Ser Thr Leu Pro Pro Ser Asn Asn Met Val Ser Ala Arg
                245                 250                 255

Val Asn Arg Gln Gln Ser Ser Asp Leu Asn Ser Ser Ser His Thr
                260                 265                 270

Asn Ser Ser Asn Asn Gln Gly Asn Phe Gly Cys Ser Pro Gly Asn Gln
                275                 280                 285

Ile Val Ala Asn Val Ala Leu Asn Gln Gly Gln Ala Gly Ser Leu Glu
                290                 295                 300

His His His His His His
305                 310
```

```
<210> SEQ ID NO 4
<211> LENGTH: 252
<212> TYPE: PRT
<213> ORGANISM: Mus musculus

<400> SEQUENCE: 4

Gln Glu Ala Cys Gln Arg Tyr Glu Val Met Gln Cys Phe Thr Val Ser
  1               5                  10                  15

Gln Pro Lys Ser Ile Gln Glu Asp Gly Glu Asp Phe Gln Ser Cys Leu
             20                  25                  30

Ile Cys Ile Ala Arg Arg Leu Pro Arg Pro Ala Ile Thr Gly Val
         35                  40                  45

Glu Ser Phe Met Thr Lys Gln Asp Thr Thr Gly Lys Ile Ile Ser Ile
 50                  55                  60

Asp Thr Ser Ser Leu Arg Ala Ala Gly Arg Thr Gly Trp Glu Asp Leu
 65                  70                  75                  80

Val Arg Lys Cys Ile Tyr Ala Phe Phe Gln Pro Gln Gly Arg Glu Pro
                 85                  90                  95

Ser Tyr Ala Arg Gln Leu Phe Gln Glu Val Met Thr Arg Gly Thr Ala
            100                 105                 110

Ser Ser Pro Ser Tyr Arg Phe Ile Leu Asn Asp Gly Thr Met Leu Ser
            115                 120                 125

Ala His Thr Lys Cys Lys Leu Cys Tyr Pro Gln Ser Pro Asp Met Gln
        130                 135                 140

Pro Phe Ile Met Gly Ile His Ile Ile Asp Arg Glu His Ser Gly Leu
145                 150                 155                 160

Ser Pro Gln Asp Asp Ser Asn Ser Gly Met Ser Ile Pro Arg Ile Asn
                165                 170                 175

Pro Ser Val Asn Pro Gly Ile Ser Pro Ala His Gly Val Thr Arg Ser
            180                 185                 190

Ser Thr Leu Pro Pro Ser Asn Asn Asn Met Val Ser Ala Arg Val Asn
        195                 200                 205

Arg Gln Gln Ser Ser Asp Leu Asn Ser Ser Ser His Thr Asn Ser
    210                 215                 220

Ser Asn Asn Gln Gly Asn Phe Gly Cys Ser Pro Gly Asn Gln Ile Val
225                 230                 235                 240

Ala Asn Val Ala Leu Asn Gln Gly Gln Ala Gly Ser
                245                 250

<210> SEQ ID NO 5
<211> LENGTH: 56
<212> TYPE: PRT
<213> ORGANISM: Homo sapiens

<400> SEQUENCE: 5

Pro Pro Leu Leu Pro Pro Thr Glu Gln Asp Leu Thr Lys Leu Leu Leu
  1               5                  10                  15

Glu Gly Gln Gly Glu Ser Gly Gly Gly Ser Leu Gly Ala Gln Pro Leu
             20                  25                  30

Leu Gln Pro Ser His Tyr Gly Gln Ser Gly Ile Ser Met Ser His Met
         35                  40                  45

Asp Leu Arg Ala Asn Pro Ser Trp
 50                  55
```

```
<210> SEQ ID NO 6
<211> LENGTH: 21
<212> TYPE: PRT
<213> ORGANISM: Homo sapiens
<220> FEATURE:
<223> OTHER INFORMATION: Part of SEQ ID 5

<400> SEQUENCE: 6

Leu Leu Pro Pro Thr Glu Gln Asp Leu Thr Lys Leu Leu Leu Glu
 1               5                  10                  15

Gly Gln Gly Glu Ser Gly
                20
```

METHOD OF IDENTIFYING SUBSTANCES WHICH MODULATE INTERLEUKIN 4(IL-4) SIGNALING

APPLICATION DATA

This application claims benefit to EP 01 117 097.4 filed Jul. 13, 2001 and U.S. provisional application 60/306,552 filed Jul. 19, 2001.

INTRODUCTION

The present invention belongs to the field of identification of pharmaceutically active substances and the use of such substances in therapy, and in particular tumor diseases and preferably in inflammatory airway diseases.

IL-4 dependent signaling plays an important role in tumor diseases and in regulation of immune and/or anti-inflammatory responses in inflammatory airway diseases, for example asthma. IL-4 regulates immune and anti-inflammatory responses. It promotes the differentiation of T helper precursors towards the Th2 lineage while inhibiting Th1 development. Furthermore, IL-4 stimulation of B cells triggers immunoglobulin class switching to IgE isotype. This recombination is thought to be initiated following the transcriptional activation of the germline ε promoter which leads to the generation of the sterile ε transcript. Most of the IL-4 regulated functions are mediated by the signal transducer and activator of transcription 6 (STAT6).

STAT6 belongs to the STAT protein family, which transmit signals from activated cytokine receptors to the nucleus. Following their cytokine-induced tyrosine phosphorylation exerted by Janus kinases (JAKs). STATs dimerize and move to the nucleus where they modulate transcription through specific DNA sequence elements (Darnell 1997; Darnell et al., 1994; Ihle 1996). So far, seven mammalian STATs have been identified (STAT1, STAT2, STAT3, STAT4, STAT5a, STAT5b, STAT6). They share the same structure of functional domains. The N-terminal portion mediates cooperative binding of multiple DNA sites (Vinkemeier et al., 1996; Xu et al., 1996). The region that determine the DNA binding site specificity is located between amino acids 400 and 500 (Horvath et al., 1995). The SH2 domain mediates association with the activated receptor (Greenlund et al., 1994; Stahl et al., 1995) and dimerization via reciprocal SH2-phospho-tyrosine interaction (Schindler et al., 1995; Shuai et al., 1994). The C-terminal part constitutes the transactivation domain (Darnell 1997; Hoey and Schindler 1998). While STAT3 and STAT5 are expressed in most cell types and activated by a variety of cytokines and growth factors, other STAT proteins play specific roles in host defenses (Darnell 1997). STAT6 is activated in response to IL-4 (Hou et al., 1994) and IL-13.

STAT6 deficient mice have defects in IL-4 mediated functions including Th2 development, induction of CD23 and MHC class II expression, immunoglobulin class switching to IgE, demonstrating the essential role of STAT6 in these IL-4 responsive induced functions (Kaplan et al., 1996; Shimoda et al., 1996). STAT6 binding sites have been identified in several of IL-4 responsive genes. They are best characterized in the Ig germline ε promoter, which contains a composite binding element for STAT6 and the CAAT/enhancer-binding protein (C/EBP) (Delphin and Stavnezer 1995). The transactivation domain of STAT6 was characterized as a modular, proline-rich region in the C-terminus of the protein. The structure of this domain is quite different from that of the other members of the STAT family (Lu et al., 1997; Moriggl et al. 1997). Two distinct C-terminal transcription activation domains, which cooperate with each other and themselves, have recently been mapped (Goenka et al., 1999). The molecular mechanism for this cooperation has not yet been defined.

Activation of transcription in general requires the recruitment of transcriptional co-activators, which are part of chromatin remodeling complexes possessing histone acetyl transferase activities and serve a bridge to the basal transcriptional apparatus (Hampsey and Reinberg 1999). Functionally conserved co-activators CREB binding protein (CBP) and p300 could be identified to be recruited by STAT6 and required for transcriptional induction by IL-4 (Gingras et al., 1999). p300/CBP are also recruited by different classes of transcription factors, including nuclear receptors (NR), AP-1, p53, p65 subunit of NFkB and STAT1, STAT2 and STAT5 (Goodman et al 2000; Pfitzner et al., 1998)

The NCOA (nuclear co-activator) family, also called p160- or SRC-(steroid receptor co-activator) co-activator family were identified as NR (nuclear receptor) binding proteins, which enhance transcriptional activation by these ligand induced transcription factors (Xu et al., 1999). Three homologous factors, termed NCoA-1/SRC-1 (Onate et al., 1995; Kamei et al.1996); NCoA-2/TIF2/GRIP1 (Voegel et al., 1996; Hong et al., 1997) and p/CIP/ACTR/AIB1 (Torchia et al., 1997; Chen et al., 1997; Anzick et al., 1997) have been identified. NCoA factors can also associate with p300/CBP (Kamei et al., 1996; Yao et al., 1996).

There is a continuous need to provide drugs for treating tumor diseases and inflammatory airway diseases. Tumor diseases and symptoms of inflammatory airway diseases can be attributed to signaling of IL-4. There is therefore a need for drugs modulating IL-4 signaling in order to eliminate a basis of said diseases and of symptoms of inflammatory processes.

DESCRIPTION OF THE INVENTION

In the present invention it is found that the biological activity of STAT6 activating gene expression in response to IL-4 is strongly enhanced by and is depending on NCoA-1 (nuclear coactivator 1) in vivo and in vitro as set forth in example 2. Surprisingly, NCoA-1 interacts directly with STAT6 whereas no other member of the NCoA co-activator family bind to STAT6. Over-expression of the STAT6 interacting domain of NCoA-1 inhibits transactivation by STAT6 in a transdominant manner. NCoA-1 binds independently to a specific part of the STAT6 transactivation domain.

The identification of the interaction of NCoA-1 with STAT6 provides a basis for a variety of applications. For example, the present invention provides a method and/or a test system to determine whether a substance can modulate, i.e. acts as an inhibitor or activator of IL-4 dependent signaling. Preferably, said substance can modulate, i.e. acts as an inhibitor or activator of a biological activity of STAT6.

Thereby the present invention also provides pharmaceutical compositions and methods for treating animals, preferably human beings suffering from a tumor disease or from an inflammatory airway disease, preferably asthma.

A "tumor disease" according to the invention is any disease which is accompanied by a development of a malignant or benignant tumor. A preferred tumor disease of the invention is Hodgkin Lymphoma.

The term "biological activity of STAT6" as used hereinafter includes, for example, an interaction of STAT6 with as well as the binding of STAT6 to factors other than STAT6 which are necessary to induce transcription. The preferred meaning of the term "biological activity of STAT6" in the context of the invention is inducing transcription as a result of IL-4 signaling, the more preferred meaning is the interaction of STAT6 with and binding to NCoA-1 resulting in forming a complex as a prerequisite to induce transcription of genes with STAT6 responsive elements, preferably in a tumor disease or in an inflammatory airway disease.

The invention also concerns functional equivalents, like naturally occurring alleles, derivatives, variants, mutants, and fragments of STAT6 having the ability to interact with as well as bind to NCoA-1. Particularly preferred in this regard is a fragment of STAT6 comprising at least amino acid 677 to 847 of STAT6 (SEQ ID NO: 2), more preferred is a fragment comprising at least amino acids 792 to 847 (SEQ ID NO: 5), and most preferred is a fragment comprising at least a fragment of SEQ ID NO: 5 spanning amino acid 794 to 814 (in the numbering system of SEQ ID NO: 5 spanning amino acid 3 to 23) as depicted in SEQ ID NO: 6. Such a fragment may be fused to another amino acid sequence. For example, such a derivative can be a fusion polypeptide comprising e.g. part of a glutathione S transferase fused to at least amino acid 677 to 847 of STAT6, as exemplified in SEQ ID No. 1.

The term "under condition where STAT6 and NCoA-1 are capable of forming a complex" used hereinafter includes but is not limited to conditions which are set forth in example 1.

The biological activity of NCoA-1 according to the present invention, i.e. enhancing a biological activity of STAT6 preferably in a tumor disease or in an inflammatory airway disease is dependent, for example, on interaction of NCoA-1 with STAT6, preferably direct binding of both proteins.

The invention also concerns functional equivalents, like naturally occurring alleles, derivatives, variants for example the homologous human amino acid sequence, mutants and fragments of NCoA-1 having the ability to interact with as well as to bind to STAT6. In a preferred embodiment, the present invention relates to a fragment of NCoA-1 comprising at least amino acid 212 to 463 of NCoA-1 as depicted in SEQ ID NO: 4. Such a fragment may be fused to an other amino acid sequence. For example, such a derivative can be a fusion polypeptide comprising e.g. a part of a thrombin protease cleavage side, a enterokinase side, and a so called histidine tag (His tag) comprising several histidine residues in a row (Janknecht et al. 1991) fused to at least amino acid 212 to 462 NCoA-1, as exemplified in SEQ ID No. 3. In a preferred embodiment, NCoA-1 or a fragment thereof is labeled with a detectable label, for example fused to a histidine tag.

In one embodiment, the present invention concerns a method which can be performed in a cellular system as well as in a cell free system for determining whether a substance is able to modulate the interaction of STAT6 with NCoA-1, preferably a method for determining whether a substance is an activator i.e. promotes the interaction of both peptides or an inhibitor i.e. prevents said interaction. This method is characterized in that STAT6 or fragments or derivatives thereof having the ability to bind to NCoA-1 are brought into contact with NCoA-1 or fragments or derivatives of NCoA-1 having the ability to bind to STAT6 under conditions where STAT6 and NCoA-1 or said fragments or derivatives are capable of forming a complex, and said complex can be used to induce a measurable readout Said readout is measured in the absence or presence of the substance of interest and obtained readouts are compared. Equal readouts determine a substance which do not modulate the said interaction whereas a readout paralleling higher amounts of said complex when compared with the readout obtained in the absence of the substance indicates a substance which can act as an activator according to the invention. A readout paralleling lower amounts indicates a substance which can act as an inhibitor according to the invention. In the present invention measuring a readout comprises techniques known in the art to detect that STAT6 and NCoA-1 or fragments or derivatives thereof according to the invention have been interacted according to the invention. For example direct detection of a formed complex according to the invention can be performed e.g. via physical methods or binding of an other molecule which recognizes the complex e.g. antibodies or the like. For said recognition unlabeled and labeled STAT6, NCoA-1 or fragments or derivatives can be used, for example one of said interacting polypeptides can be labeled with e.g. a fused histidine tag, e.g. consisting of at least five consecutive histidine residues, and recognized by a molecule which specifically binds to the tag e.g. a histidine specific antibody. Said antibody can be detected by techniques well known in the art e.g. using a second antibody which itself is linked e.g. to an enzyme which is capable of catalyzing a measurable reaction, for example by detecting reaction products like modified substrates or by-products e.g. like emitting light. Such a method can comprise steps like:

(a) binding a first polypeptide comprising at least amino acid 677 to 847 of STAT6 according to SEQ ID NO: 2, more preferably at least amino acid 792 to 847 of STAT6 according to SEQ ID NO:5, most preferably at least amino acid 794 to 814 according to SEQ ID NO:6 to a solid carrier which is present in a vessel or part of that vessel;

(b) adding a substance of interest or a mock control, optionally in a suitable solvent;

(c) adding a detectably labeled second polypeptide comprising at least amino acid 212 to 463 of NCoA-1 according to SEQ ID NO: 4, under conditions enabling both said polypeptides to bind to each other;

(d) removing unbound second polypeptide (e) measuring the amount of detectably labeled second polypeptide bound to the first polypeptide, or can comprise steps like:

(a) binding a first polypeptide comprising at least amino acid 212 to 463 of NCoA-1 according to SEQ ID NO: 4, to a solid carrier which is present in a vessel or part of that vessel;

(b) adding a substance of interest or a mock control, optionally in a suitable solvent;

(c) adding a detectably labeled second polypeptide comprising at least amino acid 677 to 847 of STAT6 according to SEQ ID NO: 2, more preferably at least amino acid 792 to 847 of STAT6 according to SEQ ID NO: 5, most preferably at least amino acid 794 to 814 according to SEQ ID NO: 6 under conditions enabling both said polypeptides to bind to each other;

(d) removing unbound second polypeptide (e) measuring the amount of detectably labeled second polypeptide bound to the first polypeptide.

The present invention concerns a test method for determining whether a substance is an activator or inhibitor of said interaction according to the invention. Since an interaction of STAT6 with NCoA-1 triggering IL-4 signaling is involved in a tumor disease or in an inflammatory airway disease and plays a role in mediating inflammation, a substance modulating the biological activity of STAT6 and or of NCoA-1 can be used for treating a tumor disease, preferably Hodgkin Lymphoma or an inflammatory airway diseases, preferably asthma, or can be used as lead compound for optimization of the function of the substance in a way that the optimized substance is suitable for treating tumor disease, preferably Hodgkin Lymphoma or inflammatory airway diseases, preferably asthma.

The present invention also concerns a test method for determining whether a substance is an activator or an inhibitor of the interaction of STAT6 with NCoA-1. A test system useful for performing a method of the invention may comprise a cellular or a cell-free system. For example, one embodiment of the invention concerns a test system that is designed in a way to allow the testing of substances acting on the interaction of STAT6 with NCoA-1 or fragments or variants or derivatives thereof according to the invention, e.g. using expression of a reporter-gene, e.g. luciferase gene or the like, as a measurable readout regulated by a STAT6 responsive element.

A method according to the invention can on the one hand be useful for high throughput testing suitable for determining whether a substance is an inhibitor or activator of the invention, but also e.g. for secondary testing or validation of a hit or lead substance identified in high throughput testing.

For performing a method of the invention, a test system according to the invention can be used.

A test system of the invention may comprises elements well known in the art. Said test system is designed in a way to measure the interaction of STAT6 with NCoA-1 or fragments or derivative according to the invention which can be performed by immobilizing one of the interacting polypeptides on a solid surface preferably on the bottom of a vessel more preferred on a ELISA plate. The other polypeptide preferably detectably labeled more preferred labeled with a histidine tag as well as the substance of interest or a mock control, optionally in a suitable solvent is added under conditions enabling both said polypeptides to bind to each other. Prior to detect the interaction of said polypeptides according to the invention, i.e. prior to the detection of the formed complex unbound polypeptides can be removed to promote detection of said complex which can be performed by measuring the amount of detectably labeled second polypeptide bound to the first polypeptide. Such a test system for determining whether a substance is an activator or an inhibitor of the interaction of STAT6 with NCoA-1 can e.g. consist of
  (a) STAT6 or fragments or derivatives thereof having the ability to bind to NCoA-1;
  (b) NCoA-1 or fragments or derivatives thereof having the ability to bind to STAT6;
  (c) a vessel wherein said STAT6 or fragments or derivatives thereof may form a complex with said NCoA-1 or fragments or derivatives thereof;
  (d) a device to measure said complex.

A said test system can include a first polypeptide which comprises at least amino acid 677 to 847 of STAT6 according to SEQ ID NO: 2, more preferably at least amino acid 792 to 847 of STAT6 according to SEQ ID NO: 5, most preferably at least amino acid 794 to 814 according to SEQ ID NO: 6 and a second polypeptide which comprises at least amino acid 212 to 463 of NCoA-1 according to SEQ ID NO: 4.

The present invention also concerns a substance determinable or determined in a method according to the invention to be an inhibitor or activator of the interaction of STAT6 with NCoA-1 according to the invention. A substance of the present invention is any compound which is capable of activating or preferably inhibiting a function of said interaction according to the invention. An example of a way to activate or inhibit a function of said interaction is by binding to one of respective polypeptides with a higher affinity and thereby blocking binding domain and/or a functional domain of at least one of said polypeptides, which can be done reversibly or irreversibly, depending on the nature of the substance applied. The invention also concerns a said substance of the invention which is e.g. an antibody or an organic or inorganic compound directly binding to or interfering with said interaction and thereby affecting STAT6's biological activity. A preferred substance according to the invention is peptide 1 (SEQ ID NO: 6) or an antibody directed against the peptide 1.

To exemplify how the skilled artisan following the teaching of the invention and using the methods of the invention can easily identify a said substance of the invention the following examples are disclosed:

As one example of a said substance of the invention the invention discloses a peptide designated as "peptide 1" (SEQ ID NO: 6), which has been identified to modulate the interaction of STAT6 with NcoA-1 using a method of the invention and has been determined as inhibitor of said interaction using a method of the invention, as set forth in Example 1a).

As another example of a said substance of the invention the invention discloses two polyclonal antibody sera directed against peptide 1. Said sera designated as "AB 1a" and "AB 1 b" had been determined as inhibitor of the interaction of STAT 6 with NcoA-1 according to the invention respectively, using a method of the invention, as set forth in Example 1b).

The present invention also relates to a substance of the invention as a medicament, i.e. for the treatment of a disease. A preferred substance is peptide 1 (SEQ ID NO: 6), or a substance consisting of at least two functional parts one of which is peptide 1 according to SEQ ID NO: 6 and the other is a molecule not hindering peptide 1 from its inhibitory function, or an antibody directed against said peptide 1, e.g. a mono-clonal antibody directed against peptide 1 or a polyclonal antibody e.g. AB 1a or AB 1b.

The present invention also relates to the use of a substance of the invention, preferably peptide 1 or an antibody directed against said peptide 1, e.g. a mono-clonal antibody directed against peptide 1 or a polyclonal antibody e.g. AB 1a or AB 1b for the treatment of a disease, preferably a tumor disease, more preferably Hodgkin Lymphoma, or preferably an inflammatory airway disease, more preferably asthma.

The present invention also relates to the use of a substance of the invention, preferably peptide 1 or an antibody directed against said peptide 1, e.g. a mono-clonal antibody directed against peptide 1 or a polyclonal antibody e.g. AB 1a or AB 1b for preparing a pharmaceutical composition for treating a disease, preferably a tumor disease, more preferably Hodgkin Lymphoma or preferably an inflammatory airway disease, more preferably asthma.

Another embodiment of the present invention relates to a pharmaceutical composition comprising at least one of the substances of to the invention determined to be an activator or an inhibitor, preferably peptide 1 or an antibody directed against said peptide 1, e.g. a monoclonal antibody directed against peptide 1 or a polyclonal antibody e.g. AB 1a or AB 1b. The composition may be manufactured in a manner that is itself known, e.g. by means of conventional mixing, dissolving, granulating, dragee-making, levigating, powdering, emulsifying, encapsulating, entrapping or lyophilizing processes.

In order to use substances activating or inhibiting according to the invention as drugs for treatment for a tumor disease or an chronic inflammatory airway disease, the substances can be tested in animal models for example an animal suffering from a tumor preferably a lymphoma or from an inflammatory airway disorder or a transgenic animal over-expressing STAT6 and or NCoA-1.

Toxicity and therapeutic efficacy of a substance according to the invention can be determined by standard pharmaceutical procedures, which include conducting cell culture and animal experiments to determine the $IC_{50}$, $LD_{50}$ and $ED_{50}$. The data obtained are used for estimating the animal or more preferred the human dose range, which will also depend on the dosage form (tablets, capsules, aerosol sprays ampules, etc.) and the administration route (for example transdermal, oral, buccal, nasal, enteral, parenteral, inhalative, intratracheal, or rectal).

A pharmaceutical composition containing at least one substance of the invention as an active ingredient can be formulated in conventional manner. Methods for making such formulations can be found in manuals, e.g. "Remington Pharmaceutical Science". Examples for ingredients that are useful for formulating at least one substance according to the present invention are also found in WO 99/18193, which is hereby incorporated by reference.

In a further aspect the invention concerns a method for treating a tumor disease according to the invention or for treating an inflammatory airway disease according to the invention. Such method comprises administering to a being, preferably to a human being, in need of such treatment a suitable amount of a pharmaceutical composition comprising at least one substance determined to be an activator or inhibitor by a method according to the invention for determining whether a substance is an activator or an inhibitor of the interaction of STAT6 with NCoA-1 according to the invention, preferably peptide 1 or an antibody directed against said peptide 1, e.g. a monoclonal antibody directed against peptide 1 or a polyclonal antibody e.g. AB 1a or AB 1b.

In an other embodiment the invention relates to a method for selectively modulating interaction of STAT6 with NCoA-1 according to the invention comprising administering a substance determined to be an activator or inhibitor said interaction, preferably peptide 1 or an antibody directed against said peptide 1, e.g. a monoclonal antibody directed against peptide 1 or a polyclonal antibody e.g. AB 1a or AB 1b.

The following example 1 is meant to illustrate the present invention, however, shall not be construed as limitation. However, the Example 1 describes most preferred embodiments of the invention.

EXAMPLES

Example 1

STAT6/NCoA-1-ELISA

The following is an illustration of how an interaction of STAT6 with NCoA-1 can be performed in order to identify a substance which can modulate said interaction.

Solutions:
  Coating buffer: 1×PBS pH 7.2
  Blocking buffer: 1×PBS pH 7.2, 5% BSA, 0.1% Tween 20
  Washing buffer: 1×PBS pH 7.2, 0.1% Tween 20
  Substrate solution: dissolve a phosphate citrate buffer tablet (Sigma) in 100 ml water to obtain 0.05 M phosphate citrate buffer pH 5,5. Dissolve a tablet of o-Phenylendiamine dihydrochloride (Sigma) in 30 ml of phosphate citrate buffer in the dark. Prior to use add 30 µl of 30% $H_2O_2$.

Recombinant Proteins:
  GST-STAT6 aa 677–847 and His-tagged NCoA-1 aa 212–463 are expressed in E. coli, purified by affinity-chromatografie and dialyzed against 1×PBS according to the art.

Sequences of Recombinant Proteins:
  GST-STAT6 aa 677–847 protein, SEQ ID NO:1
  His-tagged NCoA-1 aa 212–463, SEQ ID NO:3

Antibodies:
  1. Antibody: Penta-His, Quiagen (Cat. No. 34660)
  2. Antibody: Sheep anti Mouse Ig, HRP linked, Amersham Pharmacia (Cat. No. NA931)

Plate preparation:
  transfer 500 ng of GST-STAT6 amino acid 677-847 in 100 µl coating buffer to an ELISA plate. Seal the plate and incubate overnight at 4° C.
  wash the wells 3 times with washing buffer (200 µl) with incubating the wash solution for 5 minutes. After the last wash, remove any remaining washing buffer.
  block the plates by adding 200 µl of blocking buffer. Incubate at room temperature for 2 hours.
  wash the wells 3 times with washing buffer (200 µl) (see above).
  add substance of interest or mock control in a volume of 100 µl in washing buffer
  add 250 ng of His-tagged NCoA-1 amino acid 212-463 in a volume of 100 µl in washing buffer. Incubate for 1 hour at room temperature under constant agitation.
  wash the wells 3 times with washing buffer (200 µl) (see above).
  add the detection antibody (Penta-His Antibody, Qiagen, dilution 1:2000, in blocking buffer) in a volume of 100 µl. Incubate for 1 hour.
  wash the wells 3 times with washing buffer (200 µl) (see above).
  add the secondary antibody (Sheep-Anti-Mouse-Antibody, HRP-linked, Amersham Pharmacia, 1:2000, in blocking buffer) in a volume of 100 µl. Incubate for 1 hour.
  wash the wells 5 times with washing buffer (200 µl) (see above). Add 100 µl of substrate solution to each well. Incubate for 6 minutes in the dark. Stop the reaction by adding of 100 µl 1 N $H_2SO_4$. Determine the optical density of each well within 15 minutes, using an ELISA reader set to 450 nm.

The obtained signal gives a measure of the amount of NCoA-1, which has bound to the STAT6. This is shown in table 1.

TABLE 1

His-NCoA-1 (aa 212–463) bound to GST-STAT6 (aa 677–847) in an ELISA Assay.

| No. | coated protein | Added Partner Protein | 1. Antibody | 2. Antibody | Extinction 493 nm | s. d. |
|---|---|---|---|---|---|---|
| 1. | GST-STAT6 (677–847) | His-NCoA-1 (212–463) | α-Penta-His | α-mouse-HRP | 0.795 | 0.036 |

TABLE 1-continued

His-NCoA-1 (aa 212–463) bound to GST-STAT6 (aa 677–847) in an ELISA Assay.

| No. | coated protein | Added Partner Protein | 1. Antibody | 2. Antibody | Extinction 493 nm | s. d. |
|---|---|---|---|---|---|---|
| 2. | — | His-NCoA-1 (212–463) | α-Penta-His | α-mouse-HRP | 0.097 | 0.036 |
| 3. | GST-STAT6 (677–847) | — | α-Penta-His | α-mouse-HRP | 0.006 | 0.000 |
| 4. | — | 13 | α-Penta-His | α-mouse-HRP | 0.005 | 0.001 |
| 5. | GST-STAT6 (677–847) | His-NCoA-1 (212–463) | — | α-mouse-HRP | 0.006 | 0.000 |
| 6. | — | His-NCoA-1 (212–463) | — | α-mouse-HRP | 0.005 | 0.001 |

Description of Table 1

500 ng of E. coli expressed and affinity purified GST-STAT6 TAD (amino acid, aa 677-847) is coated to 96 well ELISA-plates as indicated. After incubation with 250 ng of E. coli expressed, affinity purified His-NCoA-1 (aa 212-463), bound protein is detected by mouse anti-His-antibody and peroxidase coupled sheep anti-mouse-antibody as indicated. In line 2, 4 and 6 no GST-STAT6 TAD (aa 677-847) is coated. In line 3 and 4 no His-NCoA-1 (aa 213-462) is added. In line 5 and 6 no anti-His-antibody is added. Conversion of peroxidase substrate O-phenylenediamine is measured at 492 nm. The average of three independent experiments with standard deviations (s.d.) are shown.

If the assay is carried out in the presence of test substances, the ability of which to disturb the interaction between STAT6 and NCoA-1 shall be determined, the signals in the presence of the test compounds can be compared to the control value e.g. in the absence of a test substance as exemplified in Example 1a) and 1b).

Example 1a

Inhibitor According to the Invention: Peptide 1

The following exemplify how the teaching of the invention leads to a substance according to the invention.

Peptide 1 is a Potent Inhibitor for the Interaction of STAT6 and NCoA-1

Figure 8A:
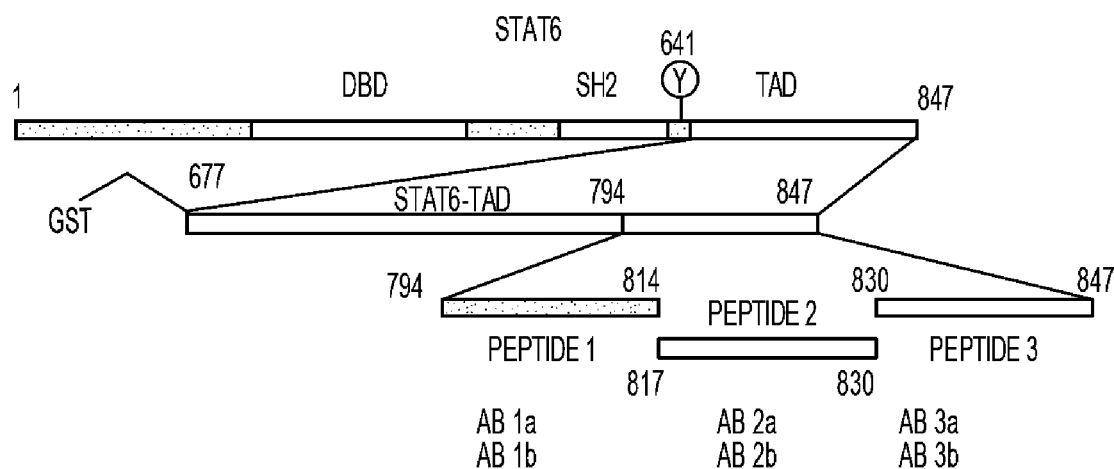

FIG. 8A) depicts the structure of i) human STAT6, ii) GST-STAT6 fusion protein (GST stands for Glutathion S Transferase), Amino acid position, DNA binding domain (DBD), SH2 domain, TAD and the cytokine-dependent phosphorylation site (Y) are indicated. iii) peptides derived from the trans-activation domain (TAD): peptide1 (amino acid 794 to 814, SEQ ID NO: 6), peptide 2 (amino acid 817 to 830), and peptide 3 (amino acid 830 to 847), and iv) depicts the designation of polyclonal rabbit anti-sera raised against said peptides respectively (AB 1a, AB 1b; AB 2a, AB 2b; AB 3a, AB 3b).

In B) results of a pull-down assay are given:

4 µg GST or GST-STAT6-TAD fusion protein purified from E. coli, are bound to 20 µl glutathione-Sepharose and are incubated with 1.5 µl [$^{35}$S]-labeled NCoA-1 in the presence of 100 µg peptide 1, or peptide 2, or peptide 3 respectively, as indicated. Material bound to the glutathione-Sepharose is recovered from the binding reaction, extensively washed and analyzed by SDS-PAGE and fluorography (lanes 2-6). Input control in lane 1 reflects 10% of the total amount of $^{35}$S -labeled NCoA-1 used in the experiments. Results reveal less binding of GST-STAT6-TAD with NCoA-1 in presence of peptide 1 (SEQ ID NO: 6) whilst presence of peptide 2 or peptide 3 does not alter the binding capacity of GST-STAT6-TAD with NCoA-1 significantly.

In C) results of an ELISA-Assay (performed according to Example 1) are given:

8 µl His-tagged NCoA-1 amino acid 212-462 (SEQ ID NO: 3) from bacterial crude lysate, which corresponds to 250 ng bound protein, are immobilized on nickel-coated ELISA plates in 100 µl coating buffer. 11,2 nmole of peptide 1, or peptide 2, or peptide 3 are added respectively as indicated. After 1 h incubation, 500 ng purified GST-STAT6-TAD are added to each reaction sample. Bound GST-STAT6-TAD is detected by an anti-GST-HRP linked antibody. As a control incubation is performed without any additional peptide (lane 4), or without immobilized His-tagged NCoA-1 (lane 5), or with the anti-GST-HRP linked antibody alone to control background binding (lane 6). Results parallel those obtained in B).

Example 1b

Inhibitor According to the Invention: Antibody AB 1a, AB 1b

The following exemplify how the teaching of the invention leads to a substance according to the invention.

Antisera Raised Against Peptide 1 Inhibit the Interaction of STAT6 with NCoA-1

Figure 9A:

FIG. 9A) gives results of a pull down assay:

4 µg GST or GST-STAT6-TAD fusion protein, bound to 20 µl glutathione-Separose, are incubated with 1.5 µl [$^{35}$S]-labeled His-tagged NCoA-1 fusion protein, comprising residues 213 to 462 (SEQ ID NO: 3). In probes 4 to 10 binding reaction is carried out in the presence of 10 µl poly-clonal rabbit anti-sera raised against a unrelated peptide (lane 4), or raised against the peptide 1 (lane 5 and 6: AB 1a, AB 1b), or the peptide 2 (lane 7 and 8: AB 2a, AB 2b), or the peptide 3 (lane 9 and 10: AB 3a, AB 3b) as indicated. Bound proteins are analyzed by SDS-PAGE and fluorography (lanes 2-10). As control, 10% of the [$^{35}$S]-labeled protein used in the experiments is analyzed in parallel (lane 1). Results indicate less binding of said STAT6 fusion protein with said NcoA-1 fusion protein in the presence of anti-sera AB 1a or AB 1b raised against the peptide 1. Remaining sera leave the protein interaction unaltered.

In B) results of an ELISA-Assay (performed according to Example 1) are given: 0,5 µl GST-STAT6-TAD fusion protein from bacterial crude lysate, which corresponds to 100 ng bound protein, are immobilized on plates which are coated with GST antibodies. Poly-clonal rabbit anti-sera raised against the peptide 1 (AB-1a, AB-1b), or the peptide 2 (AB-2a, AB-2b), or the peptide 3 (AB-3a, AB-3b) are added in a 1:1000 dilution in blocking buffer. After 1 h incubation 250 ng His-tagged-NCoA-1 fusion protein comprising amino acids 213 to 462 (SEQ ID NO: 3) purified from E. coli. is added. Bound His-NCoA-1 is detected by Penta His antibody and a subsequent secondary antibody (HRP linked sheep anti mouse antibody). As control, the binding of secondary antibody to the plates is analyzed in parallel. Results parallel the findings of A).

Example 1c

Further Characterisation of the STAT6 NcoA-1 Interaction

Point Mutations in the LXXLL Motif of STAT6-TAD Abolish the Interaction with NCoA-1 In Vitro FIG. 10A) show sequence of the peptide 1 (SEQ ID NO: 6) and its LXXLL motif. Alanin mutations introduced into the sequence are labeled by asterisk.

In B) results of a GST-pull-down assay are given:

4 µg GST or GST fusion proteins containing residues 642 to 847 of wildtype STAT6 (WT) or mutant STAT6 (mut; amino acid position 802 and 805 both L are mutated to A) are incubated with 1.5 µl [$^{35}$S]-labeled NCoA-1 fragment, comprising residues 213 to 462 (SEQ ID NO: 4) and incubated with 20 µl glutathione-Sepharose. Material bound to glutathione-Sepharose is separated by SDS-PAGE. Radiolabeled protein is detected by fluorography. Results reveal nearly no binding of said mutated STAT6 protein with said NcoA-1 protein indicating amino acid at position 802 and 805 to be essential for interaction of both proteins.

In C) controls are carried out showing that comparable amounts of said proteins are used in B): A quarter of each reaction is separately analyzed by SDS-PAGE and subsequent coomassie staining for the detection of GST and GST-STAT6 fusion proteins (WT and mut) as indicated.

Figure 11A:
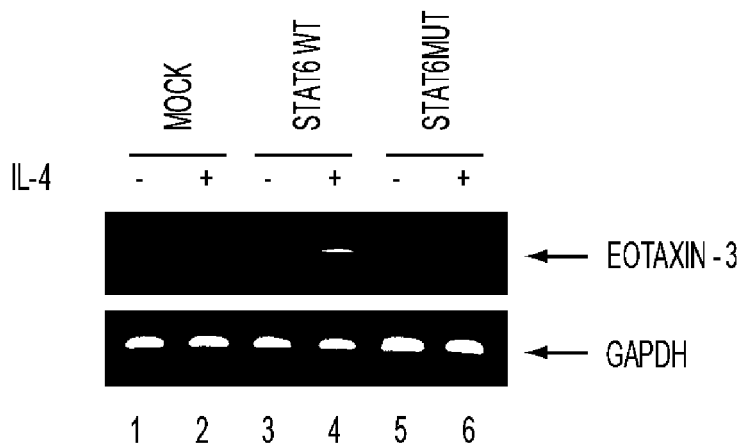

Point Mutations in the LXXLL Motif Decrease Expression of Eotaxin-3 in 293T Cells FIG. 11A) show the results of a transfection experiment and subsequent semi-quantitative analysis of Eotaxin-2 induced by IL-4 treatment:

293T cells are transfected with expression vector encoding wildtype (WT, lane 3, 4), or mutant STAT6 (mut; mutations see above: lane 4, 5), or empty expression vector (mock, lane 1, 2). Cells are induced with IL-4 for 16 hours (+) or left untreated (−) as indicated. Total RNA is prepared and expression level of Eotaxin-3 and GAPDH is analysed by RT-PCR. Results reveal decreased expression of Eotaxin-3 after IL4 stimulation in cells transfected with mutant STAT6 when compared with WT STAT6 indicating amino acid at position 802 and 805 to be essential for Eotaxin-3 expression after IL4 stimulation.

B) Amounts of secreted Eotaxin-3 from supernatants of cultured cells are determined in an ELISA type assay after transfection of 293T cells as described in A but induced with IL-4 for 48 hours (lane 2, 4, 6) or left untreated (lane 1, 3, 5). The average values with standard deviations of three independent experiments are given. Results parallel the findings of A).

In C) controls are carried out showing that comparable amounts of WT and mut STAT6 are produced in the respective transfected cells in B): Cells from B are lysed and analyzed by SDS-PAGE and Western-Blot (WB) using antibody anti-STAT6-AB or anti-β-Actin-AB as indicated.

Example 2

IL-4 Signaling Inducing STAT 6 Dependent Transcription is Enhanced by NCoA-1

The following proves NCoA-1 as an important factor in IL-4 signaling

NCoA-1 Enhances the IL-4 Induced Transcription by STAT6

Previous studies characterized the transactivation domain (TAD) of STAT6 (Lu et al., 1997; Moriggl et al., 1997) and identified autonomously trans-activating elements (Goenka et al., 1999). We have recently found that the activity of the STAT6 TAD is enhanced by the coactivators p300/CBP and observed an interaction of STAT6 with p300/CBP in vivo (Gingras et al., 1999). The region between amino acids 1850 to 2176 was characterized as the STAT6 interacting domain in p300/CBP. This domain also mediates the interaction of p300/CBP with the NCoA family of nuclear receptor coactivators (Yao et al., 1996), which together form a large coactivator complex. In order to investigate whether the SRC/NCoA coactivators are involved in the transactivation by STAT6, transient transfection assays in the IL-4-responsive liver cell line HepG2 are carried out.

Cells are transfected with a luciferase reporter construct possessing multimerized STAT6 response elements and expression vectors encoding STAT6 and the coactivators NCoA-1, NCoA-2 and p/CIP respectively (FIG. 1). After transfection the cells are treated with IL-4 or left untreated. Induction with IL-4 leads to a sixfold enhancement of basal reporter gene expression (FIG. 1, lane 1 and 2). This induction is further enhanced up to threefold when NCoA-1 is co-transfected (lane 3 and 4), whereas cotransfection of p/CIP or NCoA-2 respectively has no effect (lane 5 to 8). These results indicate that NCoA-1 is a coactivator of STAT6, whereas the other members of the NCOA family NCoA-2 and p/CIP, seem not to be involved in transactivation by STAT6.

NCoA-1 Strongly Enhances the Transactivation Potential of the C-terminal Tansactivation Domain of STAT6

To enlighten the mechanism by which NCoA-1 enhances STAT6-mediated transactivation, we investigate, whether NCoA-1 is directly targeted to STAT6 TAD. We determine the capacity of STAT6 TAD, when fused to the GAL-4 DNA binding domain (GAL4-DBD), to induce an appropriate luciferase reporter in the presence or absence of overexpressed NCoA-1. Previous studies already characterized the activity of STAT6 TAD in similar settings (Goenka, et al., 1999; Lu et al., 1997; Moriggl et al., 1997). Two GAL4 fusion proteins, possessing either the main transactivation function of STAT6 (amino acids 677 to 791) and the extreme C terminus of STAT6 (amino acids 792 to 847) (FIG. 2A) are used to investigate, whether NCoA-1 is recruited to these domains.

The various GAL4-STAT6 TAD constructs and a luciferase reporter construct containing three GAL4 response elements in its promoter region are transiently transfected into HepG2 with or without cotransfection of the coactivator NCoA-1. Expression of the isolated GAL4-DBD does not result in a significant enhancement of the luciferase reporter gene activity, which is also not effected by cotransfection of NCoA-1 (FIG. 2B, lane1 and 2). GAL4-STAT6 (677-791) strongly induces the reporter gene expression (lane 3). Cotransfection of NCoA-1 leads to a slight enhancement (lane 4). GAL4-STAT6 (792-847) does not significantly induce the reporter gene activity, indicating that this domain has a minor transactivation potential when fused to the GAL4 DBD. Surprisingly, cotransfection of NCoA-1 strongly enhances the transactivation function of the extreme C terminal domain of STAT6 to a level as high as the main transactivation domain of STAT6 (compare lane 6 and 4).

Figure 2A:
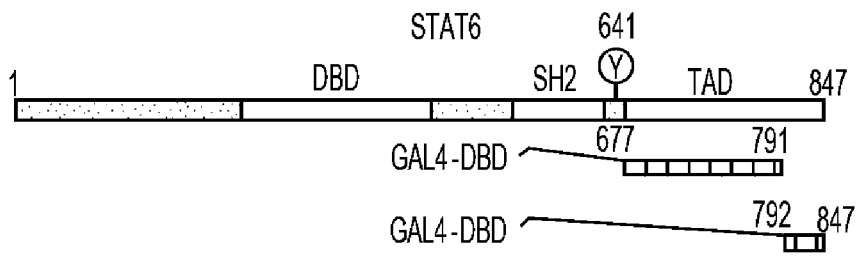
Figure 2B:
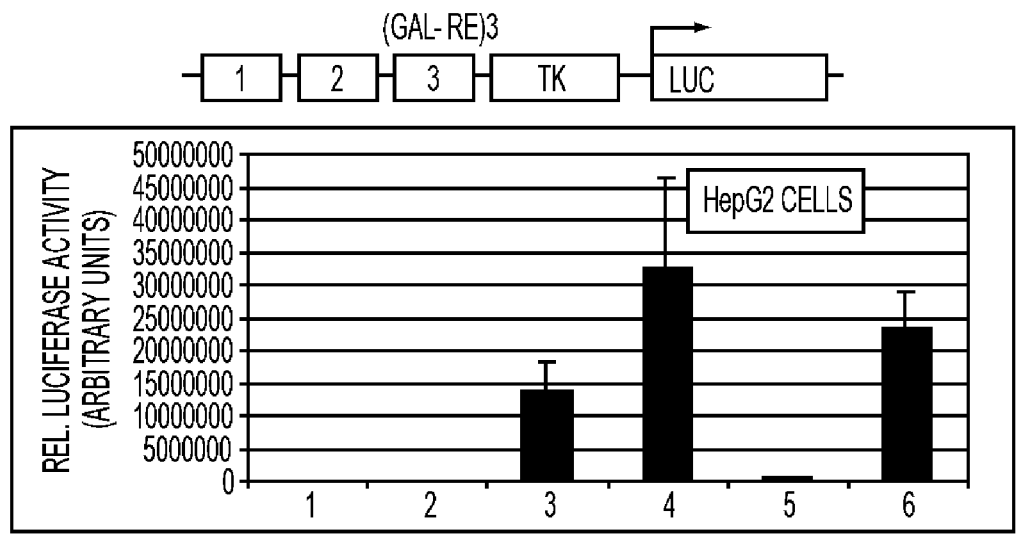
Figure 2C:
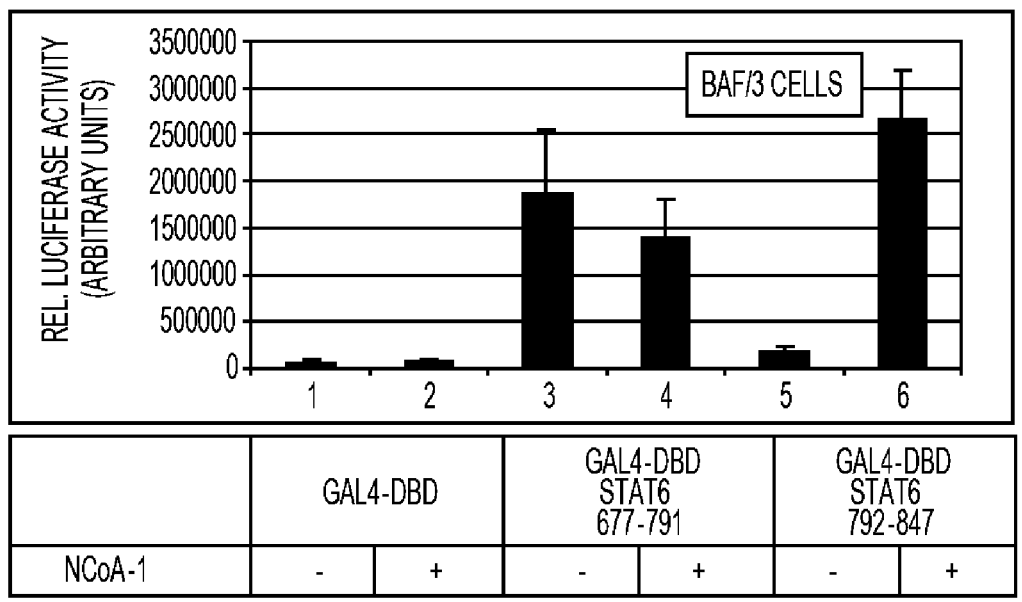

To validate this finding and to exclude that the strong effect of NCoA-1 on the transactivation activity of GAL4-STAT6 (792-847) is cell-type specific, we repeat the experiments in the pre-B-cell line Ba/F3-IL-4R (FIG. 2C). Again, GAL4-DBD alone has no significant transactivation capacity and this is not changed by coexpression of NCoA-1 (FIG. 2C, lane 1 and 2). GAL4-STAT6 (677-791) strongly induces reporter gene activity (lane 3), but in contrast to our results in HepG2 cells this is not further enhanced by coexpression of NCoA-1 (lane 4). GAL4-STAT6 (792-847) does not show significant transactivation activity by itself (lane 5). In the presence of cotransfected NCoA-1, GAL4-STAT6 (792-847) strongly enhances the transcription (lane 6). The results from these experiments confirm that NCoA-1 serves as a coactivator of the STAT6 transactivation domain. The strong coactivation effect on the far C-terminal part of the STAT6 TAD, which has very low autonomous transactivation activity, suggest that NCoA-1 is recruited to this domain. Whereas the cell type specific effect of NCoA-1 on the main transactivation domain of STAT6 (aa 677-791) might be due to an indirect recruitment of NCoA-1 to this domain by cell specific factors.

NCoA-1 and STAT6 Interact In Vivo. The Interaction Depends on the Presence of the Far C-terminal Region of STAT6

Figure 3:
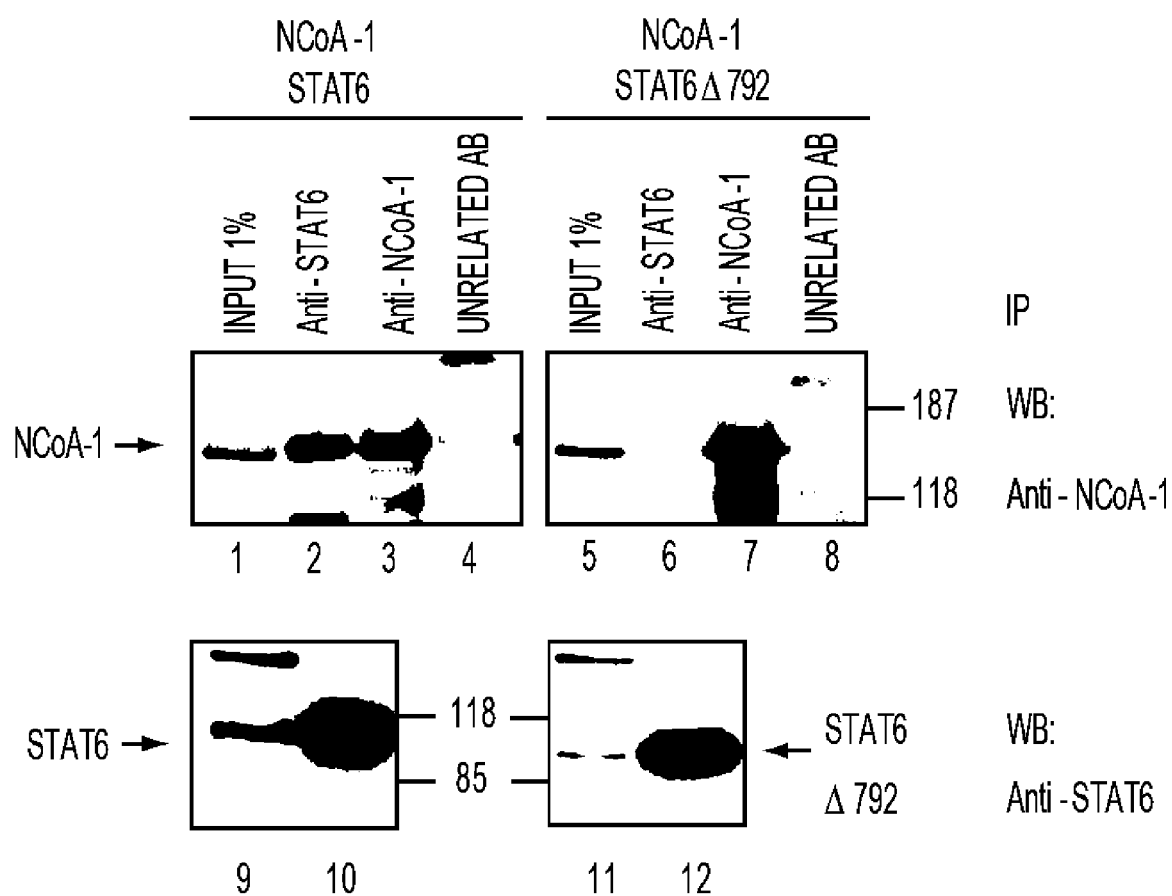

Transfection experiments illustrate that NCoA-1 strongly enhanced the transactivation potential of the far C-terminal STAT6 TA, suggesting a direct interaction between NCoA-1 and this region. To prove a likely interaction between STAT6 and NCoA-1 in vivo co-immunoprecipitation experiments are carried out. 293T cells are transfected with expression vectors encoding full length STAT6, STAT6 lacking amino acids 792-847 respectively and NCoA-1. Whole cell extracts are prepared and co-immunoprecipitation experiments are performed with the indicated antibodies. Immunoprecipitates are analyzed by Western blotting with NCoA-1 and STAT6 specific antisera. Large amount of NCoA-1 is precipitated with NCoA-1-specific antibodies (FIG. 3, lane 3 and 7). Unrelated antibodies do not precipitate NCoA-1 at all (lane 4 and 8). STAT6-specific antibodies co-immunoprecipitate nearly as much NCoA-1 as that is precipitated with the NCoA-1-specific antibodies. This is only observed when full length STAT6 is cotransfected into the cells. When the truncated form of STAT6Δ792 is present in the cells, no NCoA-1 could be co-immunoprecipitate at all (compare lane 2 and 6), although equal amounts of wild type and truncated STAT6 is precipitated in both reactions (compare lane 10 and lane 12). In summary, these experiments clearly indicate that NCoA-1 and STAT6 strongly interact in vivo and that this interaction occurs presumably through the far C-terminal region STAT6.

Figure 4:
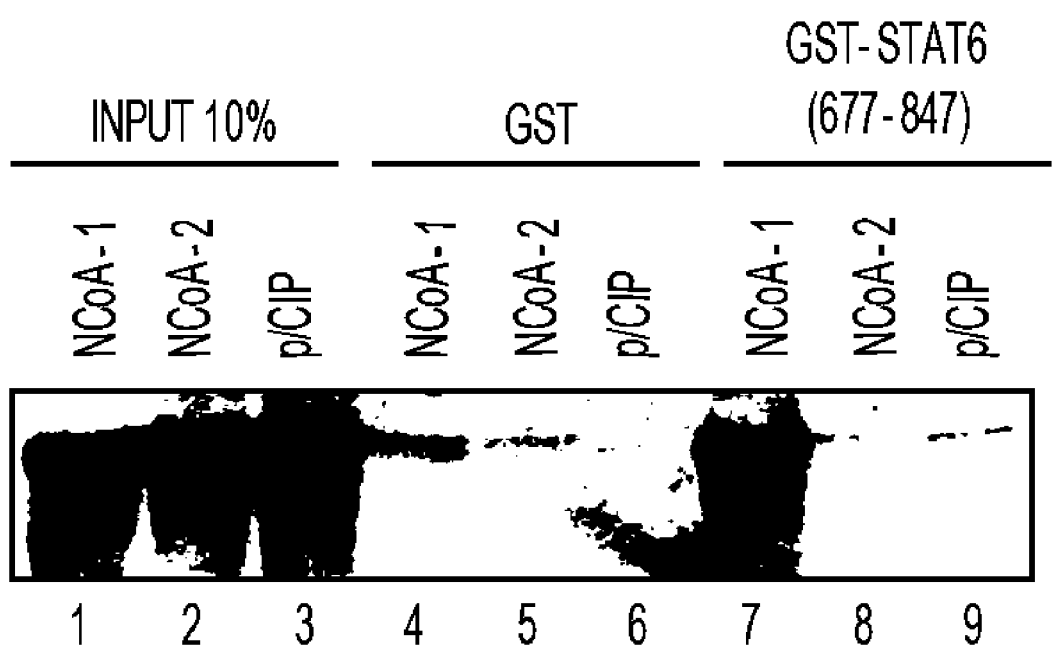

The Transactivation Domain of STAT6 Interacts with NCoA-1, but not with NCoA-2 and p/CIP In vitro To further characterize the interaction of STAT6 and NCoA-1 and to determine the specificity, GST-pull-down experiments are performed. The three related members of the NCoA/SRC-1 family are tested for interaction with the STAT6 TAD. Therefore the transactivation domain of STAT6 is fused to GST and equal amounts of GST and GST-STAT6-TAD are incubated with in vitro synthesized, [$^{35}$S]-labeled coactivators. NCoA-1 strongly binds to GST-STAT6 TAD (FIG. 4, lane 7). In contrast, NCoA-2 and p/CIP fail to interact with STAT6 TAD (lane 8, 9). No binding is observed with GST alone (lane 4, 5, 6). These findings are consistent with the transient transfection experiments shown in FIG. 1, where NCoA-1, but not NCoA-2 and p/CIP enhances transactivation by STAT6. Taken together, NCoA-1 specifically interacts with STAT6 and serves as a coactivator for STAT6.

Figure 5A:
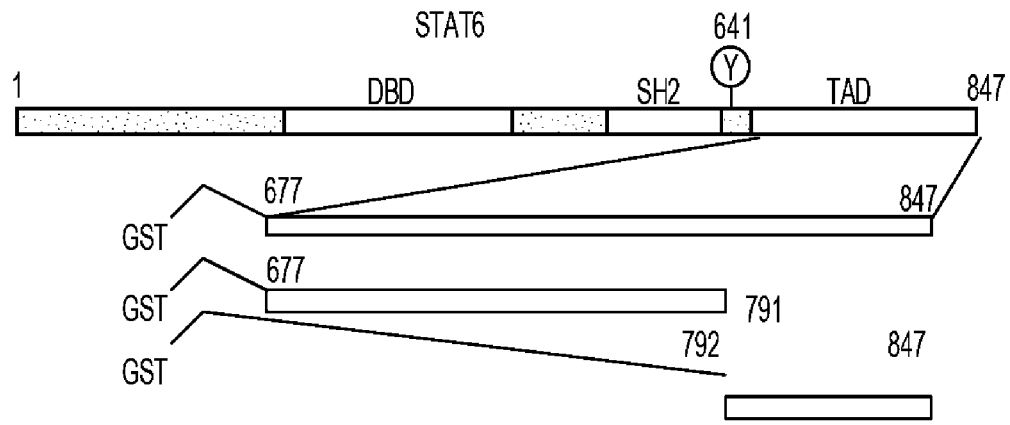
Figure 5B:
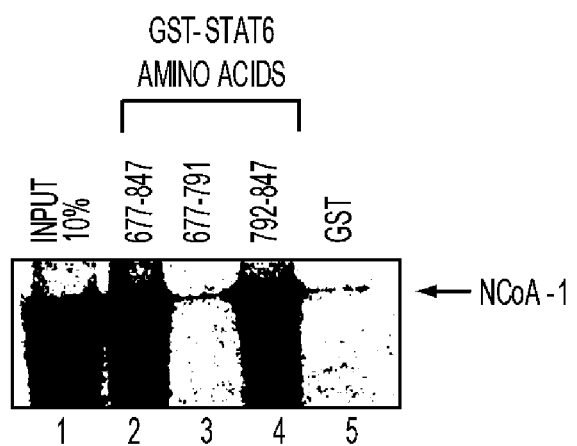
Figure 5C:
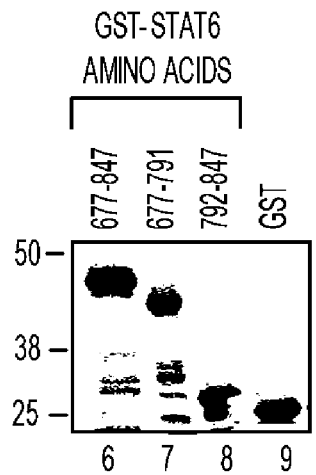

The far C-terminal Part of the STAT6 Transactivation Domain Interacts with NCoA-1 In vitro We further characterize the region in the STAT6 transactivation domain responsible for interaction. Therefore various GST-STAT6 fusion constructs representing the whole TAD (amino acids 677 to 847), the main N-terminal TAD (amino acids 677 to 791) and the far C-terminal region (amino acids 792 to 847), which strongly respond to NCoA-1, are investigated for interaction with NCoA-1 (FIG. 5A). Similar amounts of the different GST-STAT6 fusion proteins are applied as confirmed by Coomassie staining (FIG. 5C). As expected, NCoA-1 strongly interacts with GST STAT6 containing the whole TAD (FIG. 5B, lane 2). The same strong interaction is observed with GST fusion protein representing only the far C-terminal part of STAT6 TAD (lane 4), whereas the GST fusion representing the N-terminal STAT6 TAD fail to bind to NCoA-1 (lane 3). This result confirms our assumption that a direct interaction between NCoA-1 and the far C-terminal part of the STAT6 TAD is responsible for the potent coactivator function of NCoA-1.

The Transactivation Domain of STAT6 Interacts Directly with Amino Acids 212 to 462 of NCoA-1

Figure 6A:
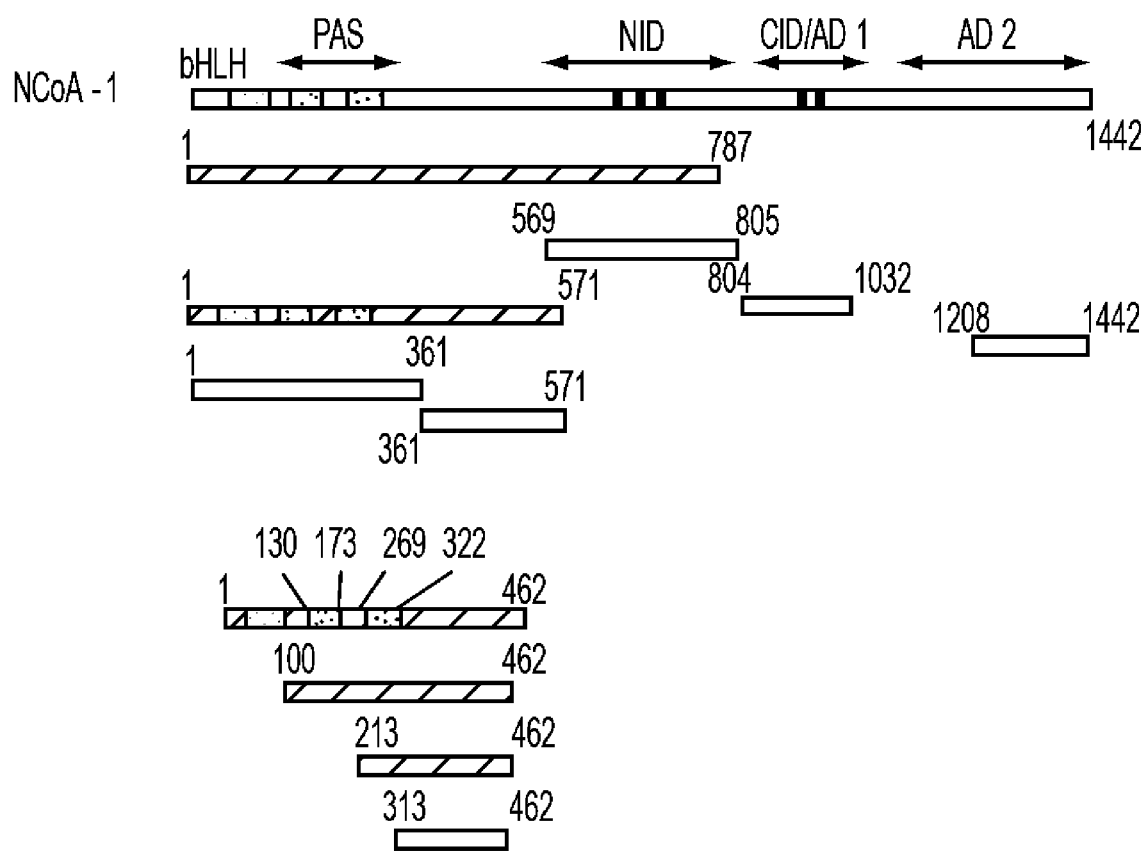

NCoA-1 contains several structural and functional domains (FIG. 6A). To investigate, which domain in NCoA-1 mediates the interaction with STAT6, we test various fragments of NCoA-1 for interaction with STAT6 in pull-down experiments (FIG. 6A). We use GST STAT6 fusion protein comprising residues 677 to 847 to analyze the binding to various fragments of in vitro translated labeled NCoA-1. We observe specific interaction of an N-terminal fragment spanning amino acids 1 to 781 (FIG. 6B, lane 11) and the full length NCoA-1 protein (lane 15) with GST-STAT6 TAD, but no interaction with GST alone (lanes 6-10). The fragments containing the nuclear receptor interaction domain (lane 12), the CBP/p300 interaction domain (lane 13) and the C-terminal transactivation domain (lane 14) fail to interact. To further narrow down the STAT6 binding site in NCoA-1, we dissect the N-terminal region of NCoA-1 and test different fragments in pulldown experiments (FIG. 6A). The divided parts (1-361 and 361-571) of the shortest N-terminal interacting fragment (1-571) fail to interact with STAT6 TA (FIG. 6C, lane 6 and 9), indicating that the binding side is somehow in between. The minimal fragment of NCoA-1, that is still able to interact with GST STAT6 possess the region from amino acids 213 to 462 which comprises the Per-Arnt-Sim (PAS) domain B and part of the serine/threonine rich domain (lane 18). Further deletion of the N-terminus (313-462, lane 21) or the C-terminus (1-361, lane 6) abolish the binding. Strong interaction is also observed when GST STAT6 is incubated with purified Histidin-tagged NCoA-1 (212-462) (data not shown), confirming that the interaction between NCoA-1 and STAT6 is direct and does not depend on additional proteins The N-terminal Region of NCoA-1 Acts as a Dominant Negative for Transcriptional Activation by STAT6

To confirm the relevance of the interaction with NCoA-1 for STAT6 transactivation, we investigate whether overexpression of the N-terminal domain of NCoA-1 (FIG. 7A) could influence the transcriptional capacity of STAT6. Therefore we express the N-terminal fragment or, as a control, the nuclear receptor interaction domain (NID) of NCoA-1 in Ba/F3-IL-4R cells and analyze their effect on the activity of the STAT6 responsive Igε-TK luciferase reporter gene. Upon induction of IL-4 a strong stimulation of the luciferase reporter gene is observed (FIG. 7B, lane 1 and 2). Coexpression of the N-terminal NCoA-1 construct containing the STAT6 interaction region abolishes this stimulation (lane 3, 4). In contrast, coexpression of the fragments harboring the NID does not show any marked effect on the STAT6-mediated stimulation (lane 5, 6).

DESCRIPTION OF FIGS. 1 TO 7 (THOSE OF FIGS. 8–11 ARE GIVEN IN EXAMPLE 1 RESPECTIVELY)

FIG. 1. NCoA-1, but not NCoA-2 and pCIP, enhances the IL-4 induced transcription by STAT6.

HepG2 cells are transfected with N4(STAT-RE)3 TK LUC reporter plasmid (2 μg), STAT6 expression vector (25 ng), NCoA-1, NCoA-2, p/CIP or empty expression vectors (200 ng) along with SV40-LacZ expression plasmid (25 ng) as a transfection control, as indicated. Transfected cells are either treated with IL-4 (10 ng/ml) for 16 hours (striped bars) or left untreated (filled bars). Cell extracts are prepared and luciferase activities are determined. The relative luciferase activities are normalized to β-galactosidase activities. Average values are given from 3 independent experiments with standard deviations.

FIGS. 2A–C. The transactivation potential of the far C-terminal transactivation domain of STAT6 is strongly enhanced by NCoA-1.

(A) Structure of human STAT6 and the fusion proteins of the GAL4-DNA binding domain (DBD) with the STAT6 transactivation domain (TAD) are shown. The GAL4-DBD (amino acids 1 to 147) is fused to different regions of STAT6 TAD. Amino acid (aa) position, DBD, SH2 domain, TAD and the cytokine-dependent phosphorylation site (Y) are indicated. (B) The reporter plasmid (GAL4-RE)3TK LUC (2 μg), expression plasmids encoding the GAL4-DBD or GAL4-DBD-STAT6-TAD fusion proteins (50 ng), NCoA-1 or empty expression plasmid (400 ng) and SV40-LacZ expression plasmid (25 ng), are transfected into HepG2 cells as indicated. (C) Ba/F3 cells are transfected with the reporter plasmid (GAL4-RE)3TK LUC (5 μg), the plasmids encoding the GAL4-DBD or GAL4-DBD-STAT6-TAD fusion proteins (50 ng), NCoA-1 (500 ng) or empty expression plasmid and SV40-LacZ expression plasmid (1 μg) as indicated. (B and C) Relative luciferase activities are determined and normalized against β-galactosidase activities. The average of three independent experiments with standard deviations are shown.

FIG. 3. NCoA-1 coimmunoprecipitaes with STAT6.

293T cells are transfected with expression vector encoding full length or truncated STAT6 along with NCoA-1 expression vector. Whole cell extracts are prepared and immunoprecipitated with STAT6-specific antibody, NCoA-1-specific antibody or unrelated antibody. All samples are analyzed by SDS-PAGE and Western blotting with antiserum against NCoA-1 (upper pannel) and STAT6 (lower pannel). An aliquot of the cell lysate corresponding to 1% of the material used for the assay is analyzed in parallel (lanes 1, 5, 9 and 11).

FIG. 4. The transactivation domain of STAT6 specifically interacts with NCoA-1 in vitro.

GST or GST-STAT6-TAD fusion protein are purified from E. coli, bound to glutathione-Sepharose and incubated with NCoA-1, NCoA-2 or p/CIP respectively, transcribed and translated in vitro in the presence of ($^{35}$S)methionine. Material bound to the glutathione-Sepharose is recovered from the binding reaction, washed extensively, and analysed by SDS-PAGE and fluorography (lanes 4-9). Input control in lanes 1-3 reflects 10% of the total amount of $^{35}$Smethionine labeled protein used in the experiments.

FIGS. 5A–C. STAT6 contacts NCoA-1 via the far C-terminal part of its transactivation domain.

(A) Structure of human STAT6 and the GST-STAT6 TAD fusion proteins. (B) NCoA-1 is labeled with ($^{35}$S)methionine by in vitro translation and incubated with glutathione-Sepharose bound GST or GST-STAT6 fusion proteins as indicated. Specifically bound material is eluted from the glutathione-Sepharose and resolved by SDS-PAGE. An aliquot of the reticulocyte lysate corresponding to 10% of the material used for the assay is analyzed in parallel (lanes 1). Radioactive labeled protein is visualized by fluorography. (C) To control the amount of GST fusion proteins in the reaction Coomassie staining is performed.

Figure 6B:
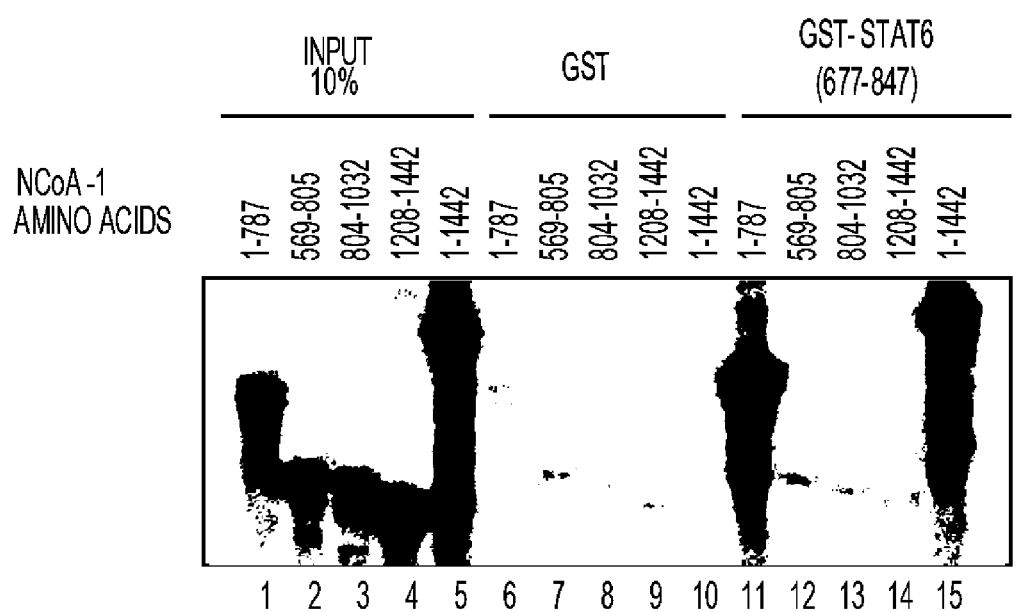
Figure 6C:
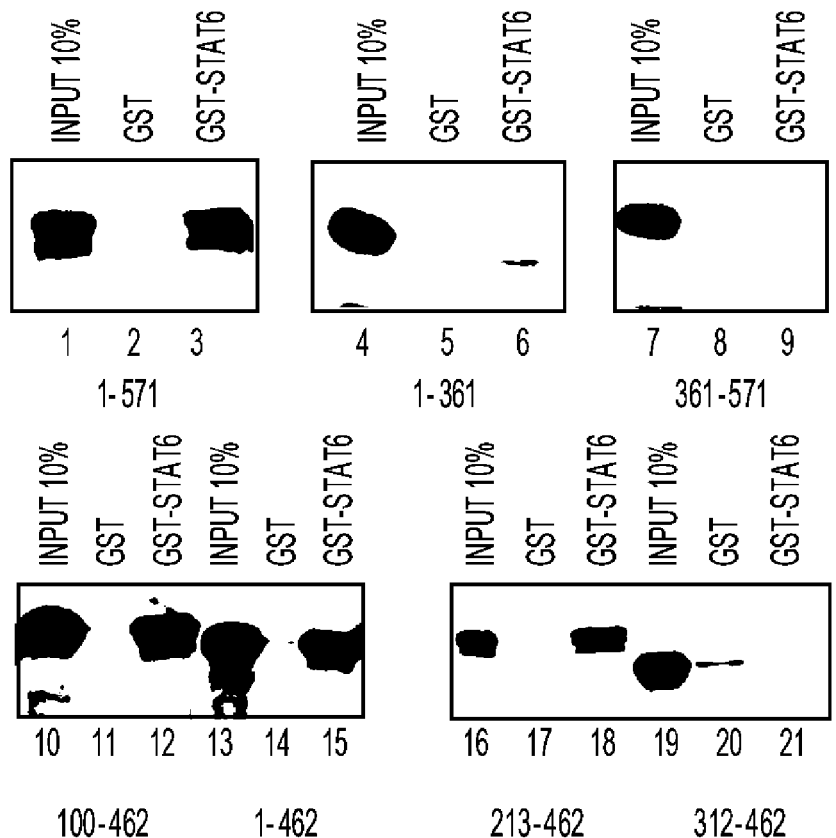

FIGS. 6A–C. The N-terminal part of NCoA-1 mediates interaction with STAT6.

(A) Schematic representation of the NCoA-1 constructs. The full-length NCoA-1 and a series of NCoA-1 deletion mutants are shown. Basic helix-loop-helix (bHLH), Per-Arnt-Sim domain (PAS), nuclear receptor interaction domain (NID), CBP interaction domain(CID)/activation domain 1 (AD1), activation domain 2 (AD2) are indicated. The amino acid numbers for each construct are shown. NCoA-1 fragments binding to STAT6 are represented with striped rectangles, non binding fragments with white rectangles. (B) and (C) NCoA-1 and a series of NCoA-1 fragments are in vitro translated in the presence of ($^{35}$S) methionine and incubated with GST alone or GST-STAT6-TAD fusion proteins bound to glutathione-Sepharose as indicated. Precipitated proteins are washed, eluted and resolved by SDS-PAGE. Aliquots of the in vitro translated NCoA-1 deletion mutants corresponding to 10% of the material used for the interaction assay are analyzed in parallel (B lanes 1-5, C lanes 1, 4, 7, 10, 16, 19). Radioactive labeled protein is visualized by fluorography.

Figure 7A:
Figure 7B:
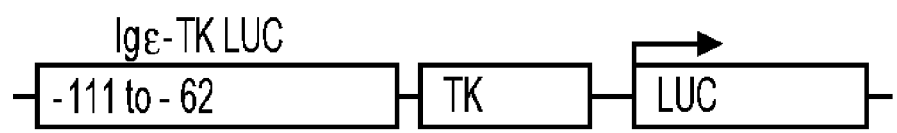
Figure 7B:
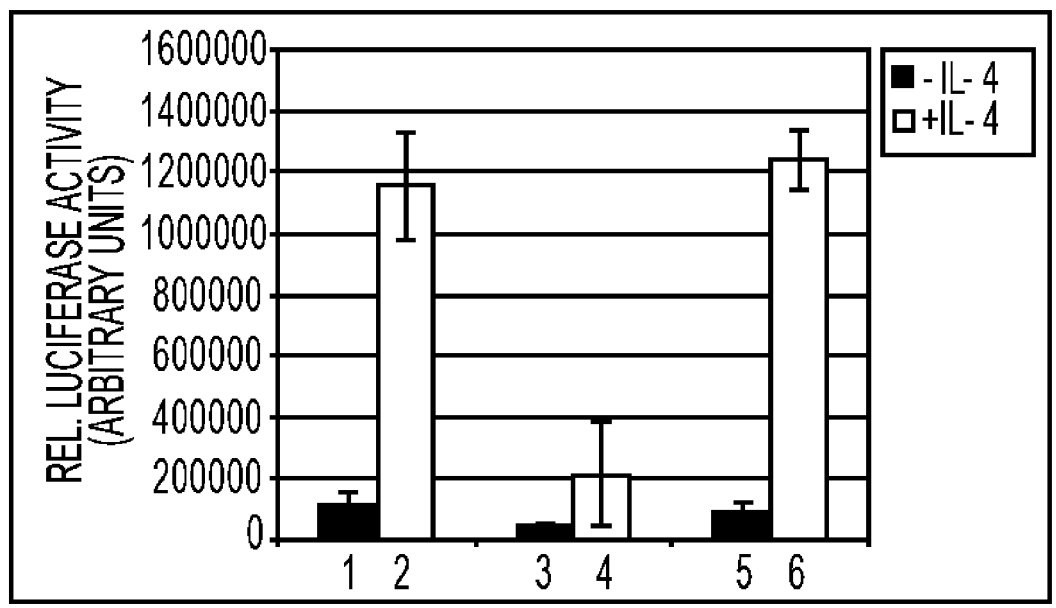

FIGS. 7A–B. The N-terminal region of NCoA-1 has a dominant negative effect on transcriptional activation by STAT6.

(A) Structure of NCoA-1. Depicted are functional and structural domains basic helix-loop-helix (bHLH), Per-Arnt-Sim domain (PAS) and nuclear receptor interaction domain (NID). (B) Ba/F3 cells are transfected with 200 ng of STAT6 expression vector, 3 μg of expression vector encoding the indicated fragments of NCoA-1 or empty vector, along with 5 μg of Igε-TK LUC reporter plasmid and 1 μg of SV40-LacZ expression vector 4 hours after transfection cells are treated with IL-4 or left untreated. 20 hours after transfection cells are harvested and luciferase activities are determined and normalized against β-galactosidase activities. The values represent the averages from three independent experiments.

Figure 8B:
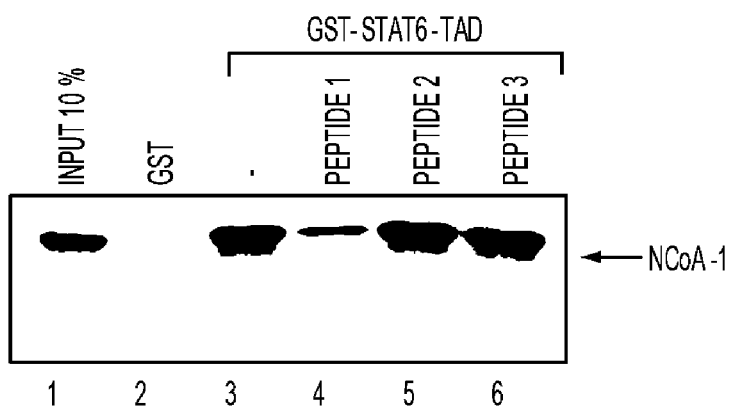
Figure 8C:
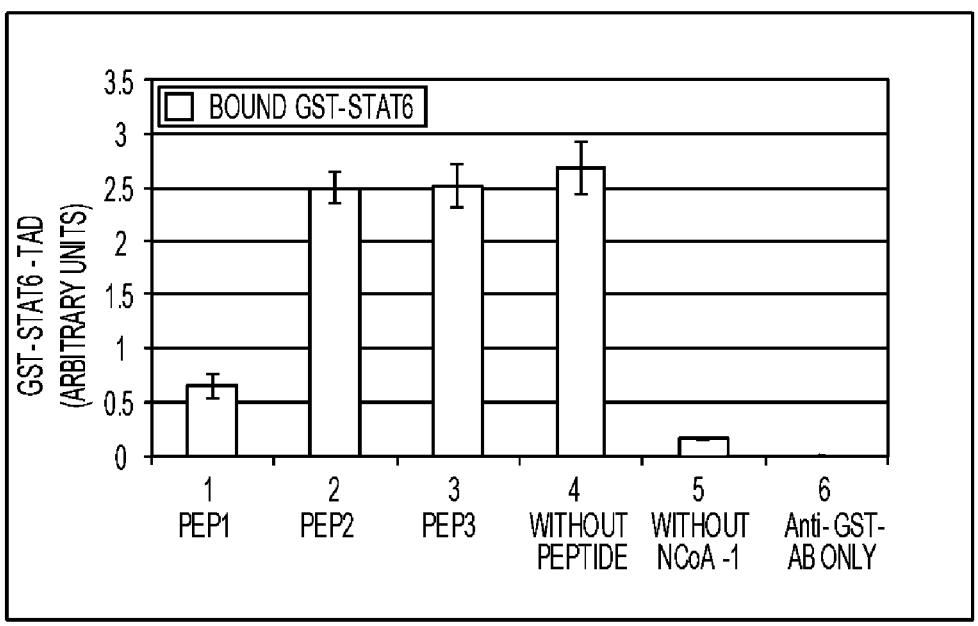

FIGS. 8A–C. Peptide 1 is a potent inhibitor for the interaction of STAT6 and NCoA-1.

(A) depicts the structure of i) human STAT6, ii) GST-STAT6 fusion protein (GST stands for Glutathion S Transferase), Amino acid position, DNA binding domain (DBD), SH2 domain, TAD and the cytokine-dependent phosphorylation site (Y) are indicated. iii) peptides derived from the trans-activation domain (TAD): peptide 1 (amino acid 794 to 814, SEQ ID NO: 6), peptide 2 (amino acid 817 to 830), and peptide 3 (amino acid 830 to 847), and iv) depicts the designation of polyclonal rabbit anti-sera raised against said peptides respectively (AB 1a, AB 1b; AB 2a, AB 2b; AB 3a, AB 3b). (B) results of a pull-down assay are given. (C) results of an ELISA-Assay (performed according to Example 1) are given.

Figure 9B:
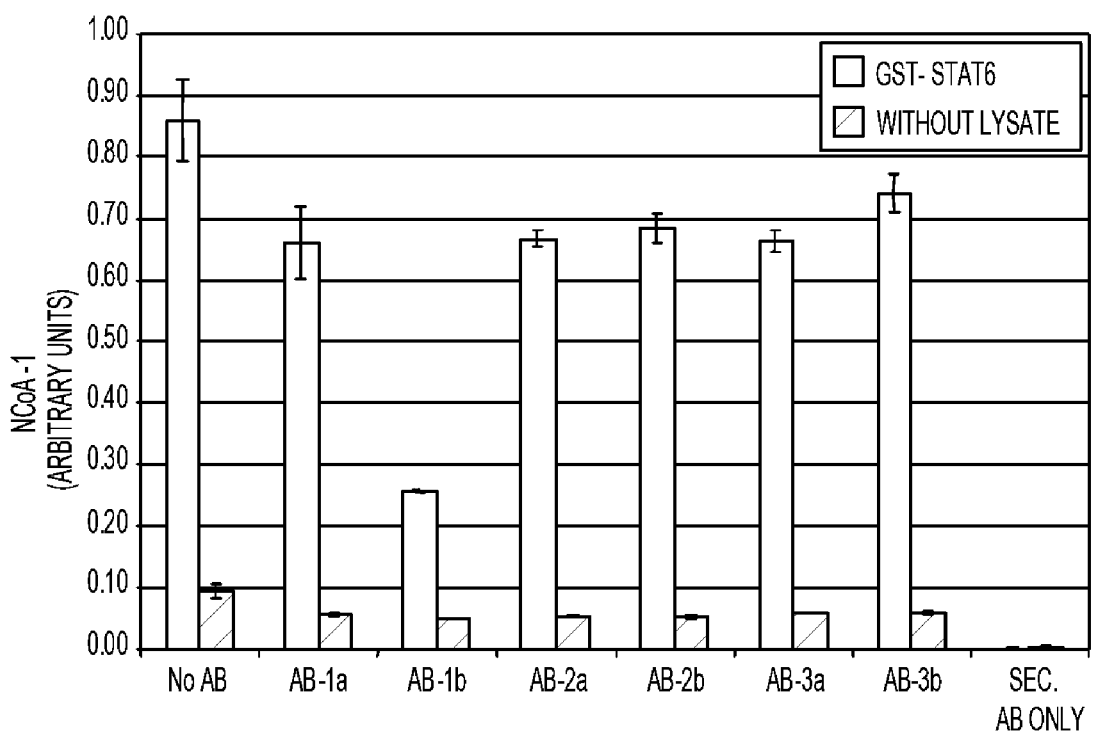

FIGS. 9A–B. Antisera raised against peptide 1 inhibit the interaction of STAT6 with NCoA-1.

(A) gives results of a pull down assay showing less binding of said STAT6 fusion protein with said NcoA-1 fusion protein in the presence of anti-sera AB 1a or AB 1b raised against the peptide 1. (B) results of an ELISA-Assay (performed according to Example 1) are given showing results parallel the findings of (A).

FIGS. 10A–C. Point mutations in the LXXLL motif of STAT6-TAD abolish the interaction with NCoA-1 in vitro.

(A) show sequence of the peptide 1 (SEQ ID NO: 6) and its LXXLL motif. Alanin mutations introduced into the sequence are labeled by asterisk. (B) results of a GST-pull-down assay are given showing nearly no binding of said mutated STAT6 protein with said NcoA-1 protein indicating amino acid at position 802 and 805 to be essential for interaction of both proteins. (C) controls are carried out showing that comparable amounts of said proteins are used in (B).

Figure 11B:
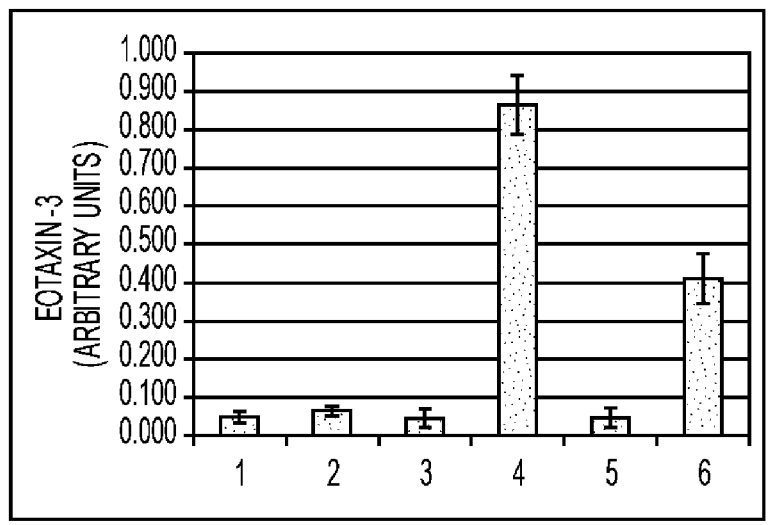
Figure 11C:
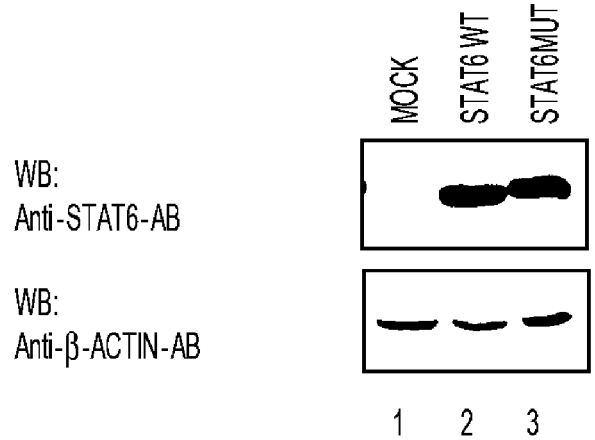

FIGS. 11A–C. Point mutations in the LXXLL motif decrease expression of Eotaxin-3 in 293T cells.

(A) show the results of a transfection experiment and subsequent semi-quantitative analysis of Eotaxin-2 induced by IL-4 treatment. (B) Amounts of secreted Eotaxin-3 from supernatants of cultured cells are determined in an ELISA type assay after transfection of 293T cells as described in A but induced with IL-4 for 48 hours (lane 2,4,6) or left untreated (lane 1,3,5). (C) controls are carried out showing that comparable amounts of WT and mut STAT6 are produced in the respective transfected cells in (B).

Literature:

Anzick, S. L., J. Kononen, R. L. Walker, D. O. Azorsa, M. M. Tanner, X. Y. Guan, G. Sauter, O. P. Kallioniemi, J. M. Trent, and P. S. Meltzer. 1997. AIB1, a steroid receptor coactivator amplified in breast and ovarian cancer. Science 277:965-8.

Chen, H., R. J. Lin, R. L. Schiltz, D. Chakravarti, A. Nash, L. Nagy, M. L. Privalsky, Y. Nakatani, and R. M. Evans. 1997. Nuclear receptor coactivator ACTR is a novel histone acetyltransferase and forms a multimeric activation complex with P/CAF and CBP/p300. Cell 90:569-80.

Darnell, J. E. 1997. STATs and gene regulation. Science 277:1630-5.

Darnell, J. E., I. M. Kerr, and G. R. Stark. 1994. Jak-STAT pathways and transcriptional activation in response to IFNs and other extracellular signaling proteins. Science 264:1415-21.

Delphin, S., and J. Stavnezer. 1995. Characterization of an interleukin 4 (IL-4) responsive region in the immunoglobulin heavy chain germline epsilon promoter: regulation by NF-IL-4, a C/EBP family member and NF-kappa B/p50. J Exp Med 181:181-92.

Gingras, S., J. Simard, B. Groner, and E. Pfitzner. 1999. p300/CBP is required for transcriptional induction by interleukin-4 and interacts with Stat6. Nucleic Acids Res 27:2722-9.

Goenka, S., J. Youn, L. M. Dzurek, U. Schindler, L. Y. Yu-Lee, and M. Boothby. 1999. Paired Stat6 C-terminal transcription activation domains required both for inhibition of an IFN-responsive promoter and trans-activation. J Immunol 163:4663-72.

Goodman, R. H., and S. Smolik. 2000. CBP/p300 in cell growth, transformation, and development. Genes Dev 14:1553-77.

Greenlund, A. C., M. A. Farrar, B. L. Viviano, and R. D. Schreiber. 1994. Ligand-induced IFN gamma receptor tyrosine phosphorylation couples the receptor to its signal transduction system (p91). Embo J 13:1591-600.

Hampsey, M., and D. Reinberg. 1999. RNA polymerase II as a control panel for multiple coactivator complexes. Curr Opin Genet Dev 9:132-9.

Hoey, T., and U. Schindler. 1998. STAT structure and function in signaling. Curr Opin Genet Dev 8:582-7.

Hong, H., K. Kohli, M. J. Garabedian, and M. R. Stallcup. 1997. GRIP1, a transcriptional coactivator for the AF-2 transactivation domain of steroid, thyroid, retinoid, and vitamin D receptors. Mol Cell Biol 17:2735-44.

Horvath, C. M., Z. Wen, and J. E. Darnell. 1995. A STAT protein domain that determines DNA sequence recognition suggests a novel DNA-binding domain. Genes Dev 9:984-94.

Hou, J., U. Schindler, W. J. Henzel, T. C. Ho, M. Brasseur, and S. L. McKnight. 1994. An interleukin-4-induced transcription factor: IL-4 Stat. Science 265:1701-6.

Ihle, J. N. 1996. STATs: signal transducers and activators of transcription. Cell 84:331-4.

Janknecht, R., de Martynoff, G., Lou, J., Hipskind, R. A., Nordheim, A., and Stunnenberg, H. G. (1991) Rapid and efficient purification of native histidine-tagged protein expressed by recombinant vaccinia virus. Proc. Natl. Acad. Sci. USA 88, 8972.

Kamei, Y., L. Xu, T. Heinzel, J. Torchia, R. Kurokawa, B. Gloss, S. C. Lin, R. A. Heyman, D. W. Rose, C. K. Glass, and M. G. Rosenfeld. 1996. A CBP integrator complex mediates transcriptional activation and AP-1 inhibition by nuclear receptors. Cell 85:403-14.

Kaplan, M. H., U. Schindler, S. T. Smiley, and M. J. Grusby. 1996. Stat6 is required for mediating responses to IL-4 and for development of Th2 cells. Immunity 4:313-9.

Lu, B., M. Reichel, D. A. Fisher, J. F. Smith, and P. Rothman. 1997. Identification of a STAT6 domain required for IL-4-induced activation of transcription. J Immunol 159:1255-64.

Moriggl, R., S. Berchtold, K. Friedrich, G. J. Standke, W. Kammer, M. Heim, M. Wissler, E. Stocklin, F. Gouilleux, and B. Groner. 1997. Comparison of the transactivation domains of Stat5 and Stat6 in lymphoid cells and mammary epithelial cells. Mol Cell Biol 17:3663-78.

Onate, S. A., S. Y. Tsai, M. J. Tsai, and B. W. O'Malley. 1995. Sequence and characterization of a coactivator for the steroid hormone receptor superfamily. Science 270:1354-7.

Pfitzner, E., R. Jahne, M. Wissler, E. Stoecklin, and B. Groner. 1998. p300/CREB-binding protein enhances the prolactin-mediated transcriptional induction through direct interaction with the transactivation domain of Stat5, but Schindler, U., P. Wu, M. Rothe, M. Brasseur, and S. L. McKnight. 1995. Components of a Stat recognition code: evidence for two layers of molecular selectivity. Immunity 2:689-97.

Shimoda, K., J. van Deursen, M. Y. Sangster, S. R. Sarawar, R. T. Carson, R. A. Tripp, C. Chu, F. W. Quelle, T. Nosaka, D. A. Vignali, P. C. Doherty, G. Grosveld, W. E. Paul, and J. N. Ihle. 1996. Lack of IL-4-induced Th2 response and IgE class switching in mice with disrupted Stat6 gene. Nature 380:630-3.

Shuai, K., C. M. Horvath, L. H. Huang, S. A. Qureshi, D. Cowburn, and J. E. Darnell. 1994. Interferon activation of the transcription factor Stat91 involves dimerization through SH2-phosphotyrosyl peptide interactions. Cell 76:821-8.

Stahl, N., T. J. Farruggella, T. G. Boulton, Z. Zhong, J. E. Darnell, and G. D. Yancopoulos. 1995. Choice of STATs and other substrates specified by modular tyrosine-based motifs in cytokine receptors. Science 267:1349-53.

Torchia, J., D. W. Rose, J. Inostroza, Y. Kamei, S. Westin, C. K. Glass, and M. G. Rosenfeld. 1997. The transcriptional does not participate in the Stat5-mediated suppression of the glucocorticoid response. Mol Endocrinol 12:1582-93.

co-activator p/CIP binds CBP and mediates nuclear-receptor function [see comments]. Nature 387:677-84.

Vinkemeier, U., S. L. Cohen, I. Moarefi, B. T. Chait, J. Kuriyan, and J. E. Darnell. 1996. DNA binding of in vitro activated Stat1 alpha, Stat1 beta and truncated Stat1: interaction between NH2-terminal domains stabilizes binding of two dimers to tandem DNA sites. Embo J 15:5616-26.

Voegel, J. J., M. J. Heine, C. Zechel, P. Chambon, and H. Gronemeyer. 1996. TIF2, a 160 kDa transcriptional mediator for the ligand-dependent activation function AF-2 of nuclear receptors. Embo J 15:3667-75.

Xu, L., C. K. Glass, and M. G. Rosenfeld. 1999. Coactivator and corepressor complexes in nuclear receptor function. Curr Opin Genet Dev 9:140-7.

Xu, X., Y. L. Sun, and T. Hoey. 1996. Cooperative DNA binding and sequence-selective recognition conferred by the STAT amino-terminal domain. Science 273:794-7.

Yao, T. P., G. Ku, N. Zhou, R. Scully, and D. M. Livingston. 1996. The nuclear hormone receptor coactivator SRC-1 is a specific target of p300. Proc Natl Acad Sci U S A 93:10626-31.

---

What is claimed is:

1. A method for determining whether a substance can modulate the binding of Signal Transducer and Activator of Transcription 6 (STAT6) with Nuclear Coactivator 1 (NCoA-1), comprising
   a) contacting STAT6 with NCoA-1 under suitable conditions where STAT6 and NCoA-1 are capable of forming a complex;
   b) measuring the binding of STAT6 to NCoA-1 in both the absence and presence of the substance;
   c) determining the ability of the substance to modulate the interaction of STAT6 with NCoA-1 by analyzing the binding of STAT6 to NCoA-1 in absence of substance in comparison with the binding in presence of substance.

2. The method according to claim 1 in which the substance can activate the binding.

3. The method according to claim 1 in which the substance can inhibit the binding.

4. The method according to claim 3, in which STAT6 is a polypeptide comprising SEQ ID NO: 2, optionally fused to another amino acid sequence.

5. The method according to claim 4, in which STAT6 is a polypeptide comprising SEQ ID NO: 1.

6. The method according to claim 3, in which STAT6 is a polypeptide comprising SEQ ID NO: 5.

7. The method according to claim 3, in which STAT6 is a polypeptide comprising SEQ ID NO: 6.

8. The method according to claim 7, in which NCoA-1 is a polypeptide comprising SEQ ID NO: 4, optionally fused to another amino acid sequence.

9. The method according to claim 8, in which NCoA-1 is a polypeptide comprising SEQ ID NO:3.

10. The method according to claim 8, in which NCoA-1 is a polypeptide, comprising SEQ ID NO: 4.

11. The method according to claim 8, wherein the STAT6 is linked to a detectable label.

12. The method according to claim 8, wherein the NCoA-1 is linked to a detectable label.

13. The method according to claims 11 or 12, wherein the label is a histidine tag consisting of at least five consecutive histidine residues.

* * * * *